US011291464B2

(12) United States Patent
Behnke-Parks et al.

(10) Patent No.: US 11,291,464 B2
(45) Date of Patent: Apr. 5, 2022

(54) SYSTEM AND METHOD FOR DETECTING AND ALIGNING ACOUSTIC BEAM IN SITU TO A TARGET USING WIDE-BEAM, LOW FREQUENCY (<1 MHZ) ULTRASOUND

(71) Applicant: Applaud Medical, Inc., San Francisco, CA (US)

(72) Inventors: William Behnke-Parks, San Francisco, CA (US); Daniel Laser, San Francisco, CA (US)

(73) Assignee: Applaud Medical, Inc., San Francisco, CA (US)

(*) Notice: Subject to any disclaimer, the term of this patent is extended or adjusted under 35 U.S.C. 154(b) by 350 days.

(21) Appl. No.: 16/473,969

(22) PCT Filed: Dec. 28, 2017

(86) PCT No.: PCT/US2017/068835
§ 371 (c)(1),
(2) Date: Jun. 26, 2019

(87) PCT Pub. No.: WO2018/126080
PCT Pub. Date: Jul. 5, 2018

(65) Prior Publication Data
US 2019/0336153 A1 Nov. 7, 2019

Related U.S. Application Data

(60) Provisional application No. 62/441,132, filed on Dec. 30, 2016.

(51) Int. Cl.
*A61B 6/00* (2006.01)
*A61B 17/225* (2006.01)
(Continued)

(52) U.S. Cl.
CPC .......... *A61B 17/2256* (2013.01); *G01S 15/42* (2013.01); *A61B 2017/00106* (2013.01); *A61N 2007/0039* (2013.01)

(58) Field of Classification Search
IPC .................. A61B 17/2256,2017/00105; A61N 2007/0039
See application file for complete search history.

(56) References Cited

U.S. PATENT DOCUMENTS 4,920,954 A * 5/1990 Alliger ............. A61B 17/22012
606/128
8,622,909 B1 * 1/2014 O'Ruanaidh ....... G01S 7/52036
600/437
(Continued)

OTHER PUBLICATIONS

International Search Report and Written Opinion for PCT/US2017/068835, dated Mar. 8, 2018 (10 pages).

*Primary Examiner* — Joel F Brutus
(74) *Attorney, Agent, or Firm* — Intrinsic Law Corp.

(57) ABSTRACT

The present invention is directed to a novel target detecting device comprising an excitation transducer generating a low frequency pulses of weakly focused ultrasonic energy and a sensing transducer. The present invention also includes a method of aligning a treatment transducer to a target by mapping the target in situ by sending a low frequency ultrasound signal and receiving reflected signals from the target. These inventions provide a simpler way of determining the location of a target and aligning a treatment transducer without the need to generate and interpret an image and then translate the image back onto the target.

65 Claims, 14 Drawing Sheets

(51) Int. Cl.
 *G01S 15/42* (2006.01)
 *A61B 17/00* (2006.01)
 *A61N 7/00* (2006.01)

(56) References Cited

U.S. PATENT DOCUMENTS

| | | | |
|---|---|---|---|
| 9,295,444 B2 | 3/2016 | Schwartz et al. | |
| 2004/0210134 A1* | 10/2004 | Hynynen | A61B 8/54 600/439 |
| 2007/0213616 A1 | 9/2007 | Anderson et al. | |
| 2008/0091125 A1* | 4/2008 | Owen | A61B 5/06 601/4 |
| 2010/0036292 A1* | 2/2010 | Darlington | A61N 7/00 601/2 |
| 2010/0137754 A1* | 6/2010 | Zhou | A61B 17/2251 601/4 |
| 2010/0280371 A1* | 11/2010 | Lacoste | A61B 8/00 600/437 |
| 2010/0310181 A1* | 12/2010 | Djeziri | G06T 7/33 382/209 |
| 2011/0054363 A1 | 3/2011 | Cain et al. | |
| 2012/0010541 A1 | 1/2012 | Cain et al. | |
| 2012/0083717 A1 | 4/2012 | Alleman et al. | |
| 2013/0123781 A1* | 5/2013 | Grubbs | A61K 41/0028 606/45 |
| 2013/0172739 A1* | 7/2013 | Paladini | A61B 6/5247 600/436 |
| 2013/0237820 A1* | 9/2013 | Vappou | A61B 8/0858 600/438 |
| 2016/0113667 A1 | 4/2016 | Bailey et al. | |
| 2016/0199034 A1* | 7/2016 | Labyed | G01S 15/8977 600/438 |

* cited by examiner

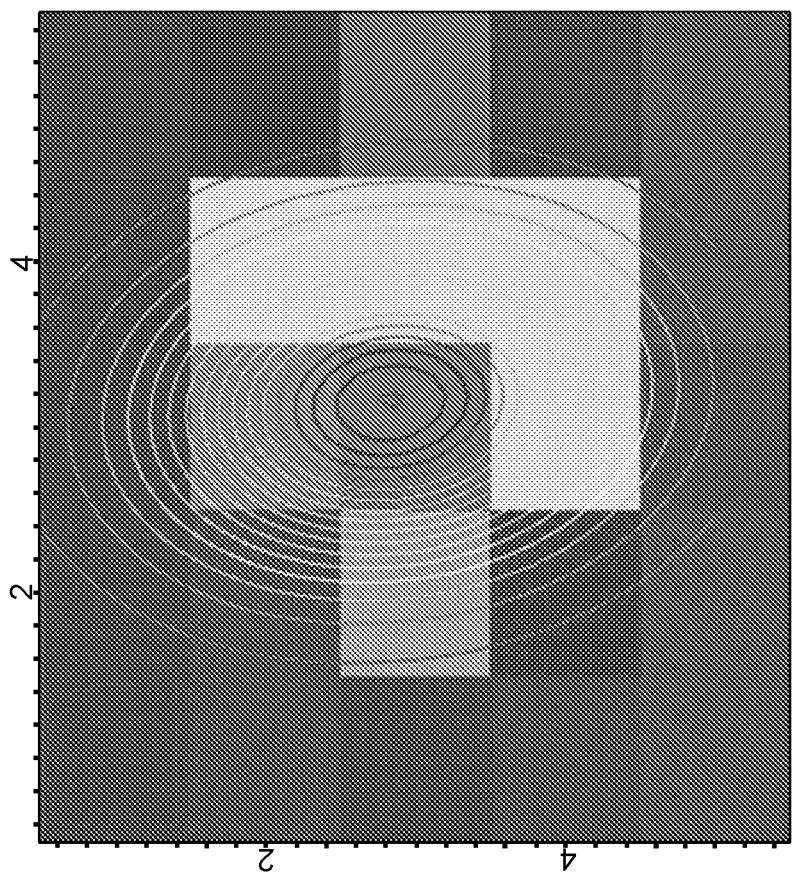
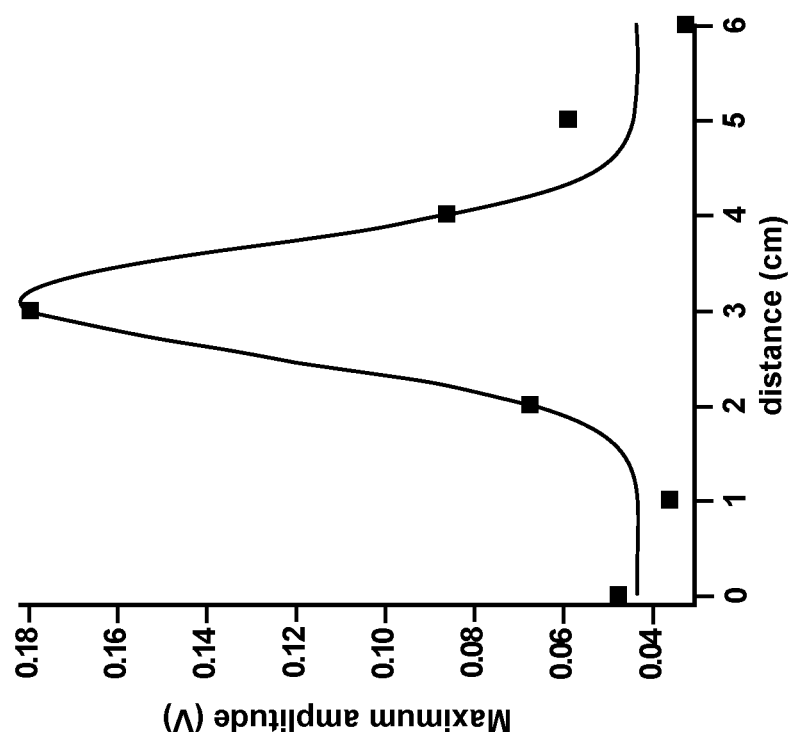
Fig. 10B
Fig. 10A

SYSTEM AND METHOD FOR DETECTING AND ALIGNING ACOUSTIC BEAM IN SITU TO A TARGET USING WIDE-BEAM, LOW FREQUENCY (<1 MHZ) ULTRASOUND

CROSS-REFERENCE TO RELATED APPLICATIONS

This application is a U.S. national stage entry of PCT/US2017/068835, filed Dec. 28, 2017, which claims the benefit of and priority to U.S. Application Ser. No. 62/441,132 filed Dec. 30, 2016, each of which is herewith incorporated by reference in its entirety.

1. BACKGROUND OF THE INVENTION

Real-time, in situ medical ultrasound typically uses an array of diffraction-limited acoustic beams with beamwidths and frequencies chosen to allow generation of a user-interpretable image of portions of anatomy or other acoustically distinctive materials and structures within an interrogated volume.

The lateral spatial resolution of an ultrasound imaging system has a lower bound, $\Delta R$:

$$\Delta R = \lambda F \qquad \text{Equation [1]}$$

where $\lambda$ is the wavelength, and F is the ratio of the aperture's focal length to its diameter. For example, for an F=1 aperture operating at 10 MHz, the lower bound on the lateral spatial resolution is given by Equation [1] as 0.3 mm.

In systems where a separate sensing transducer (e.g., a standalone hydrophone) is used to detect the transmitted pulse, the F-numbers for the excitation transducer and the sensing transducer add in reciprocal, such that the resolution is determined by the more highly-focused instrument.

Image blurring associated with imaging a target below the resolution limit can be described using a blurring function or point-spread function (PSF), where a received echo function for a target is related to the true spatial distribution of the target (e.g. as determined by a non-resolution-limited imaging system) by convolution with the blurring function.

(The widespread use of the term PSF in this sense departs from its strict definition as being limited to linear and shift-invariant imaging systems which is linear and shift invariant.) PSF is a function of factors including spatial variation in acoustic impedance in the interrogated volume and the distribution of the transmitted acoustic signal from the transducer. Therefore, while a wide distribution in transmitted acoustic pressure will ease alignment, it will also result in poor resolution and a wide distribution in the reflected sound.

Ultrasonic transducers can be configured to produce non-diffractive, non-convergent beams. An example is a transducer that produces an acoustic energy field where, for z being the coordinate axis normal to the aperture face, over a range of distances from the aperture $z_1 \leq z \leq z_2$, the variation in the non-derated instantaneous pressure at each x and y over a prescribed set of values of x and y is less than a prescribed upper limit. This type of beam is sometimes referred to as approximately collimated or weakly focused. Weakly focused beams are useful, for example, in imparting a therapeutic effect throughout an anatomical region of interest.

Given that target-locating capability can be useful even for weakly focused beams whose broad point-spread functions inherently impair target-locating capability for small targets, there is a need for means of locating small targets using weakly focused beams.

2. SUMMARY OF THE INVENTION

The present invention relates to target detection devices and methods for locating a target in situ using wide-beam, low frequency (<1 MHz) ultrasound. More specifically, some embodiments of the present invention are directed to a novel device comprising an excitation transducer capable of generating weakly focused pulses of acoustic energy, and a sensing transducer such as a hydrophone configured to receive a component of the pulses of ultrasound energy, wherein said component of the pulses of ultrasound energy can provide information about a position of the target.

The invention provides a novel and simple way of determining the location of a target, e.g., a kidney stone, a gall stone, a region of tissue calcification, a region of calcification or other biomineralization, a foreign object of sufficiently different acoustic impedance than tissue, or an accumulation of contrast agents. The invention allows targeting with or without image generation and interpretation. Therefore, this system and method is suitable for use in a wide range of settings and by persons with wide-ranging sonographic skills.

Some embodiments of the present invention provide a system for locating a target smaller than 2.3 cm in situ comprising (1) an excitation transducer emitting pulses of ultrasonic energy having one or more frequency ranging from 100 kHz to 1 MHz, wherein said ultrasonic energy is weakly focused in a volume beginning 3 cm away from an aperture and extending at least 10 cm away from the aperture; and (2) at least one sensing transducer receiving a component of the pulses of ultrasonic energy emitted by said excitation transducer upon reflection from the target, wherein said component of the pulses of ultrasonic energy is related to a position of the target.

In some embodiments, the emitted ultrasonic energy provides a non-derated instantaneous pressure at each point with an (x, y, z) coordinate, wherein the non-derated instantaneous pressure deviates less than 6 dB from a non-derated instantaneous pressure at a different point with an (x, y, z') coordinate, wherein each of the (x, y, z) and (x, y, z') is a coordinate of a point within the volume, z' is a value between 3 cm and 10 cm, and z and z' are a value for a coordinate axis normal to the aperture face.

In some embodiments, the system further comprising a moving part configured to rotate or translate the excitation transducer.

In some embodiments, the system further comprises a processor that operates on the received, reflected component of the pulses of ultrasonic energy and outputs a signal related to the position of the target.

In some embodiments, the system further comprises a treatment aligner that aligns a treatment transducer based on the signal related to the position of the target.

In some embodiments, the energy emitted from the treatment transducer is sufficient to cause breakage of the target.

In some embodiments, the excitation transducer and the treatment transducer are same. In some embodiments, the excitation transducer and the sensing transducer are same.

In some embodiments, the received, reflected component of the pulses of ultrasonic energy is not used to generate an image of the target.

In some embodiments, the processor further measures a temporal delay between emission of pulses of ultrasonic energy by the excitation transducer and reception of the reflected component of the pulses of ultrasonic energy by the at least one sensing transducer. In some embodiments, the temporal delay is used to determine the position of the target relative to the excitation transducer. In some embodiments, the temporal delay is used to determine the position of the target relative to the sensing transducer.

In some embodiments, the processor decides the position of the target based on the amplitudes of the received, reflected component of the pulses of ultrasonic energy. In some embodiments, the pulses of ultrasonic energy emitted from the excitation transducer have different amplitudes. In some embodiments, the pulses of ultrasonic energy emitted from the excitation transducer have different frequencies.

In some embodiments, maximum amplitude values of the received, reflected component of the pulses of ultrasonic energy form a distribution, wherein a centroid of the distribution correlates with a center of the target. In some embodiments, the distribution of maximum amplitude values is Gaussian, overlapping Gaussian or Airy function distribution.

In some embodiments, an average frequency of the pulses of ultrasonic energy emitted from the excitation transducer ranges from 500 kHz to 600 kHz. In some embodiments, an average frequency of the pulses of ultrasonic energy emitted from the excitation transducer ranges from 550 kHz to 600 kHz.

In some embodiments, the resolution ($\Delta R$) is larger than 0.5 mm, wherein $\Delta R$ is calculated by Equation: $\Delta R = \lambda F$, wherein $\lambda$ is an average wavelength of the purses of ultrasonic energy emitted from the excitation transducer, and F is a ratio of the aperture's focal length to the aperture's diameter. In some embodiments, the $\Delta R$ is larger than 1 mm. In some embodiments, the $\Delta R$ is larger than 2.5 mm. In some embodiments, the $\Delta R$ is larger than 5 mm.

In some embodiments, at least 80% of the ultrasonic energy emitted from the excitation transducer is confined to an insonation volume with a lateral width ranging from 1 cm to 4 cm. In some embodiments, at least 90% of the ultrasonic energy emitted from the excitation transducer is confined to an insonation volume with a lateral width ranging from 1 cm to 4 cm. In some embodiments, at least 95% of the ultrasonic energy emitted from the excitation transducer is confined to an insonation volume with a lateral width ranging from 1 cm to 4 cm.

In some embodiments, the target is selected from the group consisting of a kidney stone, a gall stone, a foreign object of sufficiently different acoustic impedance than a natural tissue, and an accumulation of contrast agents.

In some embodiments, the target is an accumulation of contrast agents, wherein the contrast agents have a specific affinity to a tissue, a cell, an organ, a foreign object, a kidney stone, a gall stone, or an atheromatous plague. In some embodiments, the contrast agents are microbubbles.

In some embodiments, the target is a kidney stone. In some embodiments, the target is a gall stone.

Some embodiments of the present invention relates to a method for locating a target smaller than 2.3 cm in situ, comprising steps of: (1) emitting pulses of ultrasonic energy having one or more frequency ranging from 100 kHz to 1 MHz by an excitation transducer, wherein said ultrasonic energy is weakly focused in a volume beginning 3 cm away from an aperture and extending at least 4 10 cm away from the aperture; and (2) receiving, by a sensing transducer, a component of the pulses of ultrasonic energy emitted by said excitation transducer upon reflection from the target, wherein said component of the pulses of ultrasonic energy is related to a position of the target.

In some embodiments, the emitted ultrasonic energy provides a non-derated instantaneous pressure at each point with an (x, y, z) coordinate, wherein the non-derated instantaneous pressure deviates less than 6 dB from a non-derated instantaneous pressure at a different point with an (x, y, z') coordinate, wherein each of the (x, y, z) and (x, y, z') is a coordinate of a point within the volume, z' is any value between 3 cm and 10 cm, and z and z' are a value for a coordinate axis normal to the aperture face.

In some embodiments, the step of emitting pulses of ultrasonic energy is done while moving the excitation transducer along the surface of a torso of a mammalian subject.

In some embodiments, the method further comprises steps of operating on the received, reflected component of the pulses of ultrasonic energy and outputting a signal related to the position of the target.

In some embodiments, the method further comprises a step of aligning a treatment transducer based on the signal related to the position of the target. In some embodiments, the method further comprises a step of emitting energy from the treatment transducer to the target. In some embodiments, the energy emitted from the treatment transducer is sufficient to cause breakage of the target.

In some embodiments, the excitation transducer and the treatment transducer are same. In some embodiments, the excitation transducer and the sensing transducer are same.

In some embodiments, the received, reflected component of the pulses of ultrasonic energy is not used to generate an image of the target.

In some embodiments, the method further comprises a step of measuring a temporal delay between emission of the pulses of ultrasonic energy by the excitation transducer and reception of the reflected component of the pulses of ultrasonic energy by the sensing transducer. In some embodiments, the temporal delay is used to determine the position of the target relative to the excitation transducer. In some embodiments, the temporal delay is used to determine the position of the target relative to the sensing transducer.

In some embodiments, the method further comprises the step of determining the position of the target based on the amplitudes of the received, reflected component of the pulses of ultrasonic energy.

In some embodiments, the pulses of ultrasonic energy emitted from the excitation transducer have different amplitudes. In some embodiments, the pulses of ultrasonic energy emitted from the excitation transducer have different frequencies.

In some embodiments, maximum amplitude values of the reflected component of the pulses of ultrasonic energy form a distribution, wherein a centroid of the distribution correlates with a center of the target. In some embodiments, the distribution of maximum amplitude values is Gaussian distribution, overlapping Gaussian or Airy function distribution.

In some embodiments, an average frequency of the pulses of ultrasonic energy emitted from the excitation transducer ranges from 500 kHz to 600 kHz. In some embodiments, the average frequency of the pulses of ultrasonic energy emitted from the excitation transducer ranges from 550 kHz to 600 kHz.

In some embodiments, the resolution $\Delta R$ is larger than 0.5 mm, wherein the $\Delta R$ is calculated by Equation: $\Delta R = \lambda F$, wherein $\lambda$ is an average wavelength of the purses of ultrasonic energy emitted from the excitation transducer, and F is a ratio of the aperture's focal length to the aperture's diameter. In some embodiments, the ΔR is larger than 1 mm, 2.5 mm, or 5 mm.

In some embodiments, at least 80%, 90%, or 95% of the ultrasonic energy emitted from the excitation transducer is confined to an insonation volume with a lateral width ranging from 1 cm to 4 cm.

In some embodiments, the target is selected from the group consisting of a kidney stone, a gall stone, a region of tissue calcification, a region of calcification or other biomineralization, a foreign object of sufficiently different acoustic impedance than a natural tissue, and an accumulation of contrast agents. In some embodiments, the target is a kidney stone.

In some embodiments, the target is an accumulation of contrast agents, wherein the contrast agents have a specific affinity to a tissue, a cell, an organ, a foreign object, a kidney stone, a gall stone, or an atheromatous plague. In some embodiments, the contrast agents are microbubbles. In some embodiments, the method further comprises a step of administering the microbubbles to a mammalian subject.

In some embodiments, the method further comprises the steps of analyzing variations of amplitudes of the emitted pulses of ultrasonic energy and the received, reflected component of the pulses of ultrasonic energy, and identifying a Mie-scatterer when the received, reflected component has a larger variation than the emitted pulses of ultrasonic energy. Increased variation in the reflected amplitude can be interpreted as the result of Mie-scattering from an object of size comparable to the wavelength of the sound field ($1 < 2\pi a/\lambda < 10$).

3. BRIEF DESCRIPTION OF THE SEVERAL VIEWS OF THE DRAWINGS

These and other features, aspects, and advantages of the present invention will become better understood with regard to the following description, and accompanying drawings, where:

FIG. 10A is a graphical representation of values determined by analyzing pulse-echo data to represent a target's location. FIG. 10B is a color-code representation of the values in FIG. 10A.

Figure 12A:
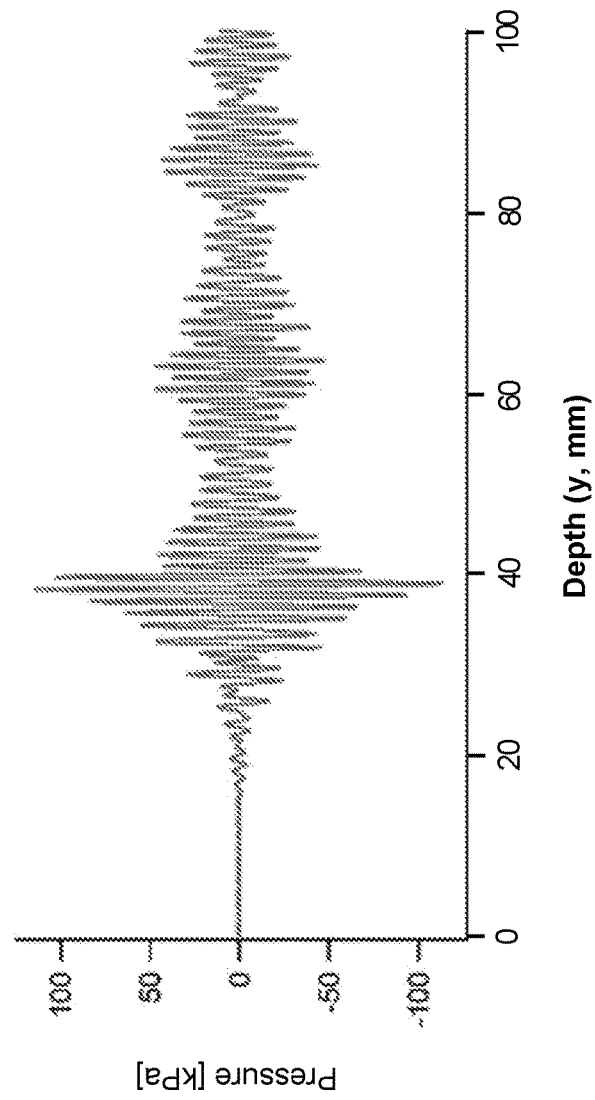
Figure 12B:
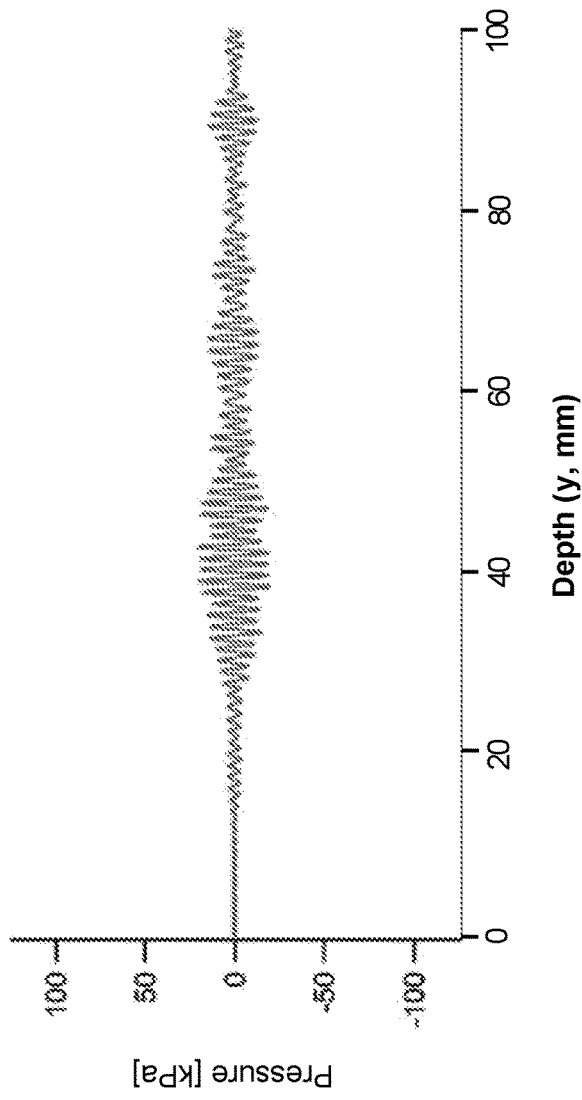

FIG. 12A provides representative pressure echoes (kPa) versus depth (g) measured for $\alpha=-4$ degrees along the cranial-caudal axis. FIG. 12B provides representative pressure echoes (kPa) versus depth (g) measured for $\alpha=-15$ degrees along the cranial-caudal axis.

Figure 13A:
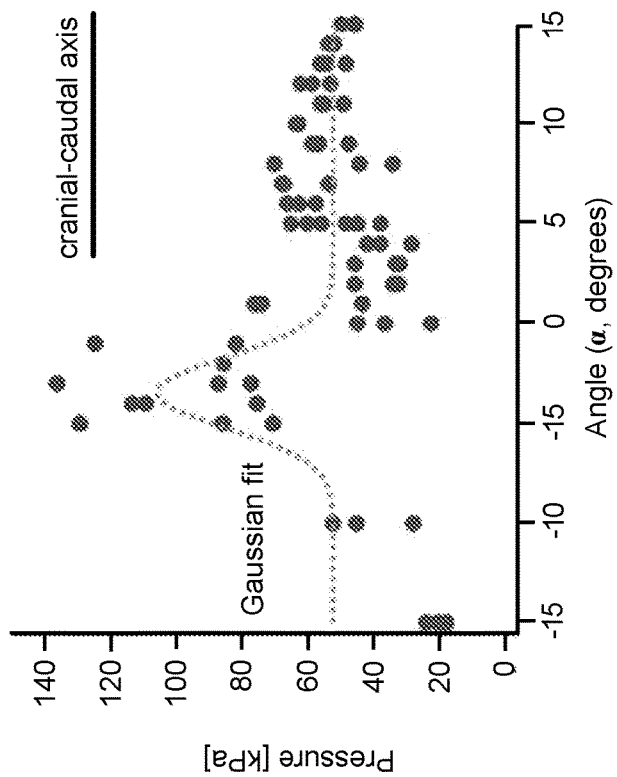
Figure 13B:
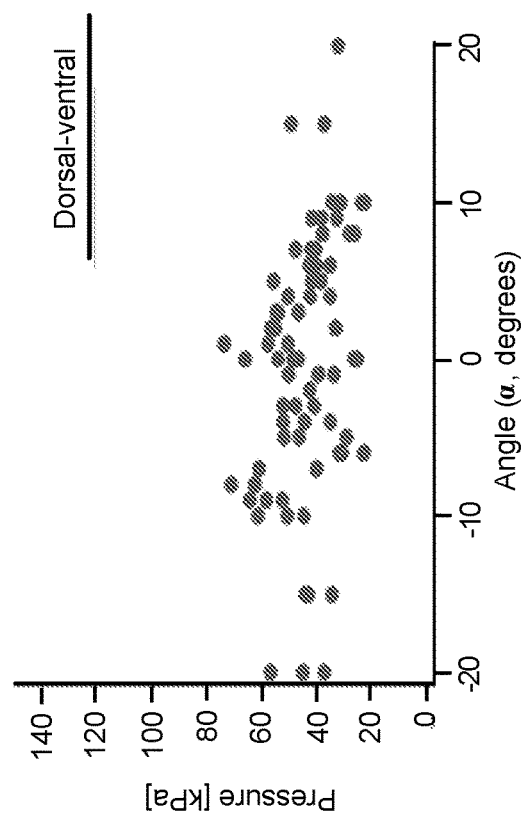

FIG. 13A is a graph presenting the recorded pressure echoes as a function of angle (a, degrees) with respect to the surface along the cranial-caudal axis. FIG. 13B is a graph presenting the recorded pressure echoes as a function of angle ($\alpha$, degrees) with respect to the surface along the dorsal-ventral axis.

Figure 14B:
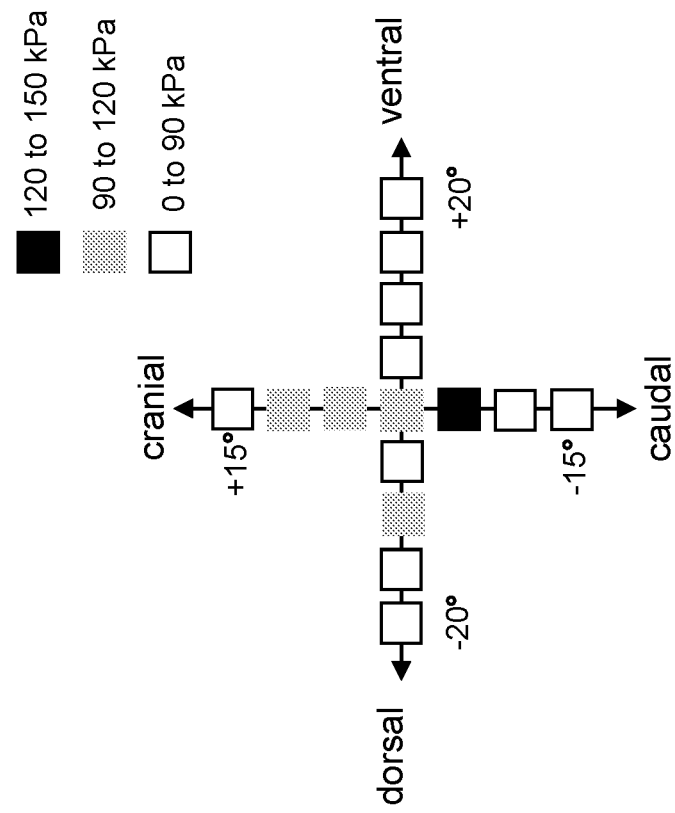
Figure 14A:
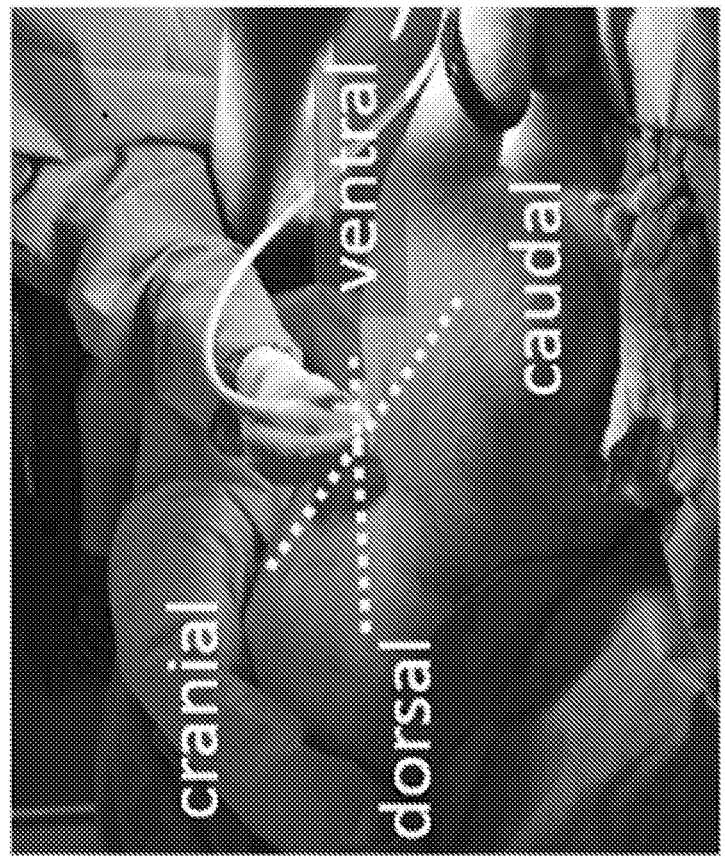

FIG. 14A is a picture of the swine model for testing the present invention in vivo with overlaid dorsal-ventral and cranial-caudal axes. FIG. 14B is a color-coded representation of maximum pressure echoes measured along the dorsal-ventral and cranial-caudal axes.

4. DETAILED DESCRIPTION OF THE INVENTION

A. Definitions

Terms used in the claims and specification are defined as set forth below unless otherwise specified. Further, if any term or symbol used herein is not defined as set forth below, it shall have its ordinary meaning in the art.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "in vivo" refers to processes that occur in a living organism.

The term "in situ" refers to processes that occur in the original, natural, or existing place or position.

The term "ex situ" refers to processes that occur outside, off site, or away from the natural location.

The term "target" when used in the present specification, refers to objects present within a biological structure, in situ, within a subject, whose position can be determined using the device and methods of the present invention. Exemplary targets include a kidney stone, a gall stone, a region of tissue calcification, a region of calcification or other biomineralization, a foreign object of sufficiently different acoustic impedance than tissue, an accumulation of contrast agents (targeted or untargeted), etc.

The term "approximately collimated" or "weakly focused" refers to an energy state where a non-derated instantaneous pressure at each x and y (within a prescribed range of x and y) is deviated less than a prescribed upper limit from non-derated pressures corresponding to the x and y across a range of z values within an insonation volume, wherein the z is a coordinate axis normal to the aperture face.

B. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

When methods of the present invention comprise multiple steps, the multiple steps are not required to be performed in a specific order, unless otherwise indicated. Descriptions or claims provided herein do not directly or indirectly require a particular order.

C. Devices and Systems for Locating a Target In Situ

The present invention is directed to a fundamentally novel device using a wide-beam, low frequency (<1 MHz) ultrasound than other devices used in the current state of the art, which gives it a technical advantage via an improved signal-to-background. It is also fundamentally different in implementation as compared to the multitude of ultrasound imaging techniques, because it detects a target such as a kidney stone, a gall stone, a foreign object of sufficiently different acoustic impedance than tissue, an accumulation of contrast agents (targeted or untargeted) and maps the location of the target without generating an image. This allows for a lower level of skill in use, comparable to a stud-finder.

Mapping is defined herein as in situ detection of a target without generation and interpretation of an image, in contrast to imaging defined to be generating an ex situ representation which requires an additional step of translating that image back onto the subject. The difference between imaging and mapping can be clarified by specifying that in the case of mapping, the reflection of sound (echo) from the target is more diffuse than the size of the object or the detector, and so multiple reads are required, from which a pattern emerges that is concentric with the surface position which is closest to the kidney stone.

Figure 1:
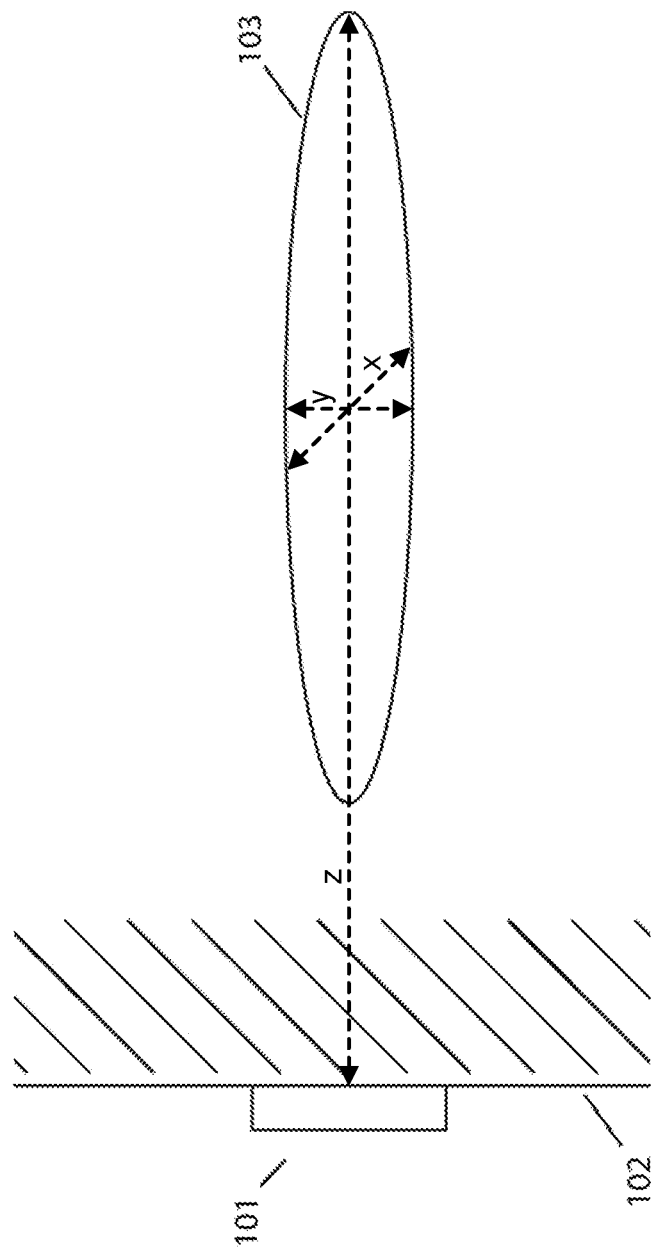
FIG. 1 is a schematic illustration of an exemplary excitation transducer on a surface generating a weakly focused ultrasound beam.

The general concept of a weakly focused ultrasound beam is illustrated in FIG. 1. An excitation transducer 101 is held against a surface 102. The term, "weakly focused ultrasound beam" refers to a state where the non-derated instantaneous pressure within the volume 103 is within a prescribed variation from a nominal value.

In some embodiments, the volume starts at least 3 cm away from the aperture and extends at least 4 cm. In some embodiments, the volume starts at least 2, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, 10.5 cm, 11 cm, 11.5 cm, 12 cm, 12.5 cm, 13 cm, 13.5 cm, 14 cm, 14.5 cm, 15 cm, 15.5 cm, 16 cm, 16.5 cm, 17 cm, 17.5 cm, 18 cm, 18.5 cm, 19 cm, or 20 cm form the aperture and extends at least 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, or 10 cm away from the aperture. In some embodiments, the volume ends at least 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, 10.5 cm, 11 cm, 11.5 cm, 12 cm, 12.5 cm, 13 cm, 13.5 cm, 14 cm, 14.5 cm, 15 cm, 15.5 cm, 16 cm, 16.5 cm, 17 cm, 17.5 cm, 18 cm, 18.5 cm, 19 cm, 19.5 cm, or 20 cm away from the aperture.

In some embodiments, the non-derated instantaneous pressure at each x and y (within a prescribed range of x and y) is deviated less than 6 dB from non-derated pressures corresponding to the x and y within the volume across a range of z values beginning at z=3 cm, wherein the z is a coordinate axis normal to the aperture face. (FIG. 1)

In some embodiments, the z value ranges between 3 cm and 7 cm. In some embodiments, the z value ranges between 3 cm and 8 cm. In some embodiments, the z value ranges between 3 cm and 9 cm. In some embodiments, the z value ranges between 3 cm and 10 cm. In some embodiments, the z value ranges between 3 and 11 cm, between 3 and 12 cm, between 3 and 13 cm, between 3 and 14 cm, between 3 and 15 cm, between 3 and 16 cm, between 3 and 17 cm, between 3 and 18 cm, between 3 and 19 cm, between 3 and 20 cm, between 4 and 8 cm, between 4 and 9 cm, between 4 and 10 cm, between 4 and 11 cm, between 4 and 12 cm, between 4 and 13 cm, between 4 and 14 cm, between 4 and 15 cm, between 4 and 16 cm, between 4 and 17 cm, between 4 and 18 cm, between 4 and 19 cm, between 4 and 20 cm, between 5 and 9 cm, between 5 and 10 cm, between 5 and 11 cm, between 5 and 12 cm, between 5 and 13 cm, between 5 and 14 cm, between 5 and 15 cm, between 5 and 16 cm, between 5 and 17 cm, between 5 and 18 cm, between 5 and 19 cm, between 5 and 20 cm, between 6 and 10 cm, between 6 and 11 cm, between 6 and 12 cm, between 6 and 13 cm, between 6 and 14 cm, between 6 and 15 cm, between 6 and 16 cm, between 6 and 17 cm, between 6 and 18 cm, between 6 and 19 cm, between 6 and 20 cm, between 7 and 11 cm, between 7 and 12 cm, between 7 and 13 cm, between 7 and 14 cm, between 7 and 15 cm, between 7 and 16 cm, between 7 and 17 cm, between 7 and 18 cm, between 7 and 19 cm, between 7 and 20 cm, between 8 and 12 cm, between 8 and 13 cm, between 8 and 14 cm, between 8 and 15 cm, between 8 and 16 cm, between 8 and 17 cm, between 8 and 18 cm, between 8 and 19 cm, between 8 and 20 cm, between 9 and 13 cm, between 9 and 14 cm, between 9 and 15 cm, between 9 and 16 cm, between 9 and 17 cm, between 9 and 18 cm, between 9 and 19 cm, between 9 and 20 cm, between 10 and 14 cm, between 10 and 15 cm, between 10 and 16 cm, between 10 and 17 cm, between 10 and 18 cm, between 10 and 19 cm, between 10 and 20 cm, between 11 and 15 cm, between 11 and 16 cm, between 11 and 17 cm, between 11 and 18 cm, between 11 and 19 cm, or between 11 and 20 cm.

In some embodiments, x and y values range between 0 and at least 0.5 cm, 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, or 10 cm. In some embodiments, x and y values range between 0 and less than 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, or 20 cm.

In some embodiments, the non-derated instantaneous pressure at each x and y (within a prescribed range of x and y) is deviated less than 4.5 dB, 5 dB, 5.5 dB, 6 dB, 6.5 dB, 7 dB, 7.5 dB, 8 dB, 8.5 dB, 9 dB, 9.5 dB, 10 dB, 10.5 dB, 11 dB, 11.5 dB, 12 dB, 13 dB, 13.5 dB, 14 dB, 14.5 dB, 15 dB, 15.5 dB, 16 dB, 16.5 dB, 17 dB, 17.5 dB, 18 dB, 18.5 dB, 19 dB, 19.5 dB or 20 dB from the non-derated pressures corresponding to the x and y within the volume across a range of z values.

The present invention counter-intuitively, further relies on the use of lower frequency sound waves (i.e., sub MHz frequencies), that reduce spatial resolution (500 kHz would have a minimum 3 mm resolution according to the diffraction limit) (as compared to frequencies used for imaging ultrasound applications) and improve the ability to detect reflections from targets such as, e.g., kidney stone-sized objects, gall stones, foreign objects of sufficiently different acoustic impedance than tissue, and accumulations of contrast agents (targeted or untargeted) by reducing reflections from the surrounding tissue (background). This background arises from cellular structures that are of a comparable size to the wavelength used in imaging techniques (f=5 to 10 MHz, $\lambda$, =0.3 mm). The physics of scattering is wavelength dependent; when the size of the scattering object is much smaller than the wavelength, the probability of scattering is drastically reduced.

Some embodiments of the present invention rely on use of sound waves with low frequencies which range from 100 kHz to 1 MHz, from 200 kHz to 1 MHz, from 300 kHz to 1 MHz, from 400 kHz to 1 MHz, from 500 kHz to 1 MHz, from 600 kHz to 1 MHz, from 100 kHz to 900 kHz, from 200 kHz to 900 kHz, from 300 kHz to 900 kHz, from 400 kHz to 900 kHz, from 500 kHz to 900 kHz, from 600 kHz to 900 kHz, from 100 kHz to 800 kHZ, from 200 kHz to 800 kHz, from 300 kHz to 800 kHz, from 400 kHz to 800 kHz, from 500 kHz to 800 kHz, from 600 kHz to 800 kHz, from 100 kHz to 700 kHz, from 200 kHz to 800 kHz, from 300 kHz to 800 kHz, from 400 kHz to 800 kHz, from 500 kHz to 800 kHz, from 600 kHz to 800 kHz, from 100 kHz to 700 kHz, from 200 kHz to 700 kHz, from 300 kHz to 700 kHz, from 400 kHz to 700 kHz, from 400 kHz to 600 kHz, from 500 kHz to 600 kHz, from 100 kHz to 600 kHz, from 200 kHz to 600 kHz, from 300 kHz to 600 kHz, from 400 kHz to 600 kHz, from 500 kHz to 600 kHz, or from 550 kHz to 600 kHz.

In some embodiments, acoustic pulses emitted from an excitation transducer comprise sound waves with one or more frequencies. In some embodiments, acoustic pulses emitted from the transducer comprise sound waves with one or more amplitudes.

Because sound waves used in the present invention have much lower frequencies than the frequencies of sound waves used by typical imaging ultrasound applications, devices and systems disclosed in the present invention provide lower spatial resolutions. When resolution is calculated using the Equation [1] (i.e., $\Delta R=\lambda F$), $\lambda$ is the wavelength of the sound wave and F is the F-number of the acoustic system, the resolutions provided by the low frequency waves are larger than 0.3 mm. In some embodiments, the resolution ($\Delta R$) is larger than 0.4 mm, larger than 0.5 mm, larger than 0.6 mm, larger than 0.7 mm, larger than 0.8 mm, larger than 0.9 mm, larger than 1 mm, larger than 2 mm, larger than 2.5 mm, larger than 3 mm, larger than 5 mm, larger than 10 mm, larger than 15 mm, larger than 20 mm, larger than 23 mm, larger than 25 mm, or larger than 30 mm.

D. Methods for Locating a Target In Situ

In some embodiments of the present invention, the ultrasound device is placed on the surface of a torso of a human or an animal subject suspected of having a target, e.g., a kidney stone, a gall stone, a region of tissue calcification, a foreign object of sufficiently different acoustic impedance than tissue, an accumulation of contrast agents (targeted or untargeted). The device sends an acoustic pulse, and then receives the reflection (echo). The amplitude of this reflected signal, within a certain temporal window as measured from the start of the pulse, is recorded. The amplitude of the reflections for a set of positions can be used to construct a map, either by an internal computer integral to the device or by a user with sufficient proficiency, which allows to determine (1) the presence/absence of the target (e.g., a kidney stone) to be ascertained, and (2) the position of the target to be localized with sufficient accuracy so that the device can be aligned with the target in situ. Lastly, the contours of the map can be analyzed for a concentric distribution, resulting in a more precise localization of the target.

Figures 2A, 2B:
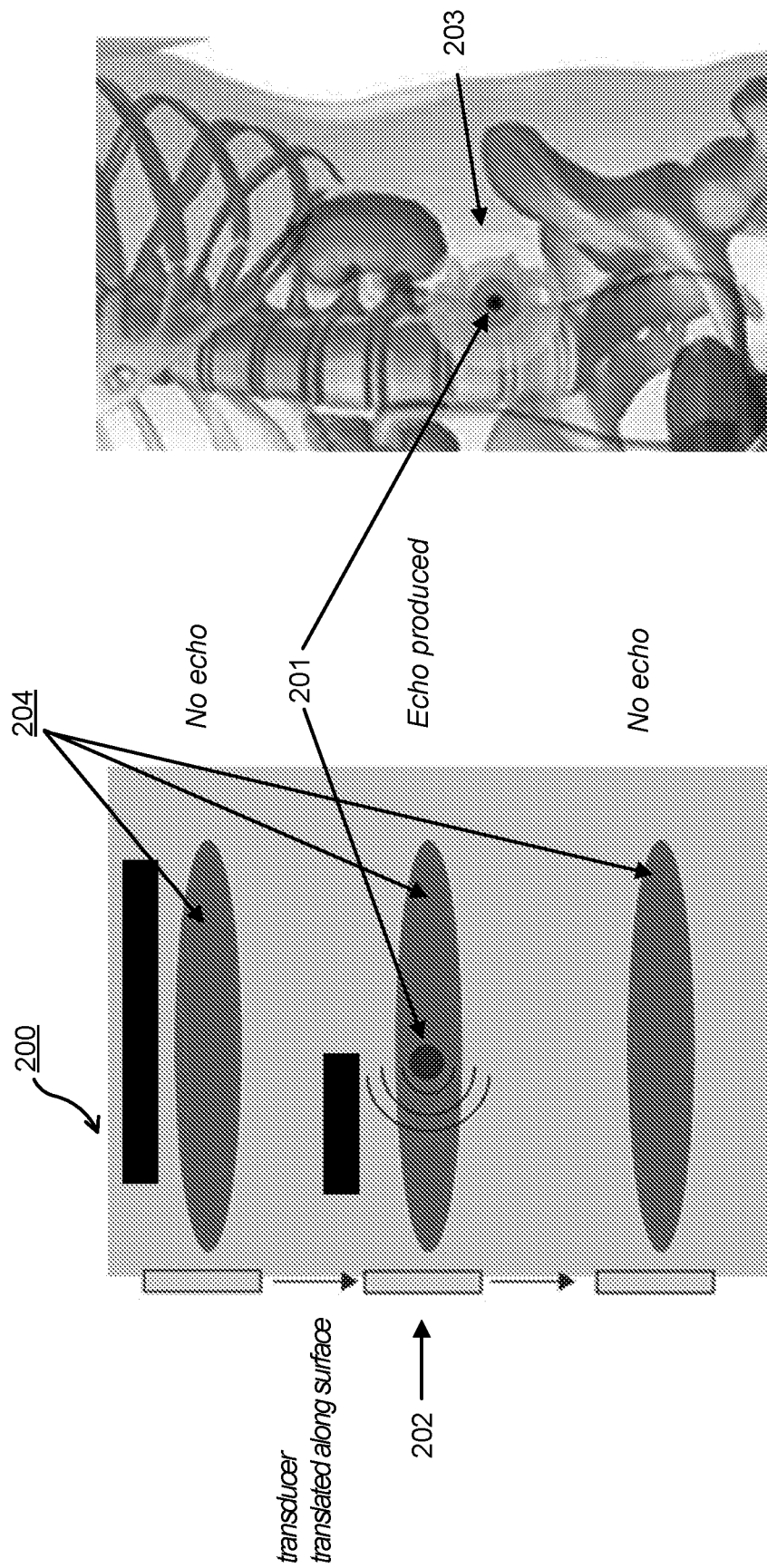
FIG. 2A is a schematic illustration of an excitation transducer translating along the surface of a torso and emitting weakly focused ultrasound beams, along with the reflection when the excitation transducer positions such that the beam encompasses a target.
FIG. 2B shows a 2D cross-section of a torso with a target reflecting a component of the weakly focused ultrasound beams.

The general concept of locating a target using a weakly focused ultrasound beam is illustrated in FIGS. 2A-B. FIG. 2A shows an excitation transducer 202 generating a weakly focused ultrasound beam while it translates along the surface of a torso 200. The non-derated instantaneous pressure within a cylindrical profile (i.e., the volume or the insonation volume) 204 is within a prescribed variation from a nominal value. Sound waves produced by the excitation transducer are peaked in the center. The width of distribution in intensity can be defined as the full-width-half-maximum (FWHM). In some embodiments, the ultrasonic energy emitted from the excitation transducer is predominantly confined to an insonation volume with a lateral width ranging from 1 cm to 4 cm, 1 cm to 4.5 cm, 1 cm to 5 cm, 1 cm to 6 cm, 1 cm to 10 cm, 0.5 cm to 4 cm, 0.5 cm to 5 cm, 0.5 cm to 6 cm, 0.6 cm to 7 cm, 1.5 cm to 5 cm, 1.5 cm to 6 cm, 1.5 cm to 7 cm, or 2 cm to 7 cm. In some embodiments, more than 70%, 80%, 90%, 95%, 98% or 99% of ultrasonic energy emitted from the transducer are confined to an insonation volume with a lateral width ranging from 1 cm to 4 cm, 1 cm to 4.5 cm, 1 cm to 5 cm, 1 cm to 6 cm, 1 cm to 10 cm, 0.5 cm to 4 cm, 0.5 cm to 5 cm, 0.5 cm to 6 cm, 0.6 cm to 7 cm, 1.5 cm to 5 cm, 1.5 cm to 6 cm, 1.5 cm to 7 cm, or 2 cm to 7 cm.

Echoes are produced from a target object 201 located at a depth (relative to the aperture face) within a range of depths where the energy of the weakly focused beam is above a prescribed minimum value. A distribution 203 can be produced by analyzing the echoes associated with multiple transducer positions and/or angles.

The target object 201 detected and located in situ using methods of the present invention can be smaller than 2.3 cm. In some embodiments, the target object 201 detected and located in situ using methods of the present invention is smaller than 0.5 cm, 1 cm, 1.3 cm, 1.5 cm, 1.8 cm, 2 cm, 2.3 cm, 2.5 cm, 2.8 cm, 3 cm, 3.3 cm, 3.5 cm, 3.8 cm, 4 cm, 4.3 cm, 4.5 cm, 4.8 cm, or 5 cm.

A user can move the transducer 202 along the surface of the subject including the target, e.g., the surface of a torso of a mammalian subject. The lateral translations of this device will produce a change in the intensity of incident waves striking a target 201. The hydrophone acceptance angle is ideally concentric with the transmitted signal from the transducer 202, or it can be acentric, resulting in a small aberration in localization.

Figure 3:
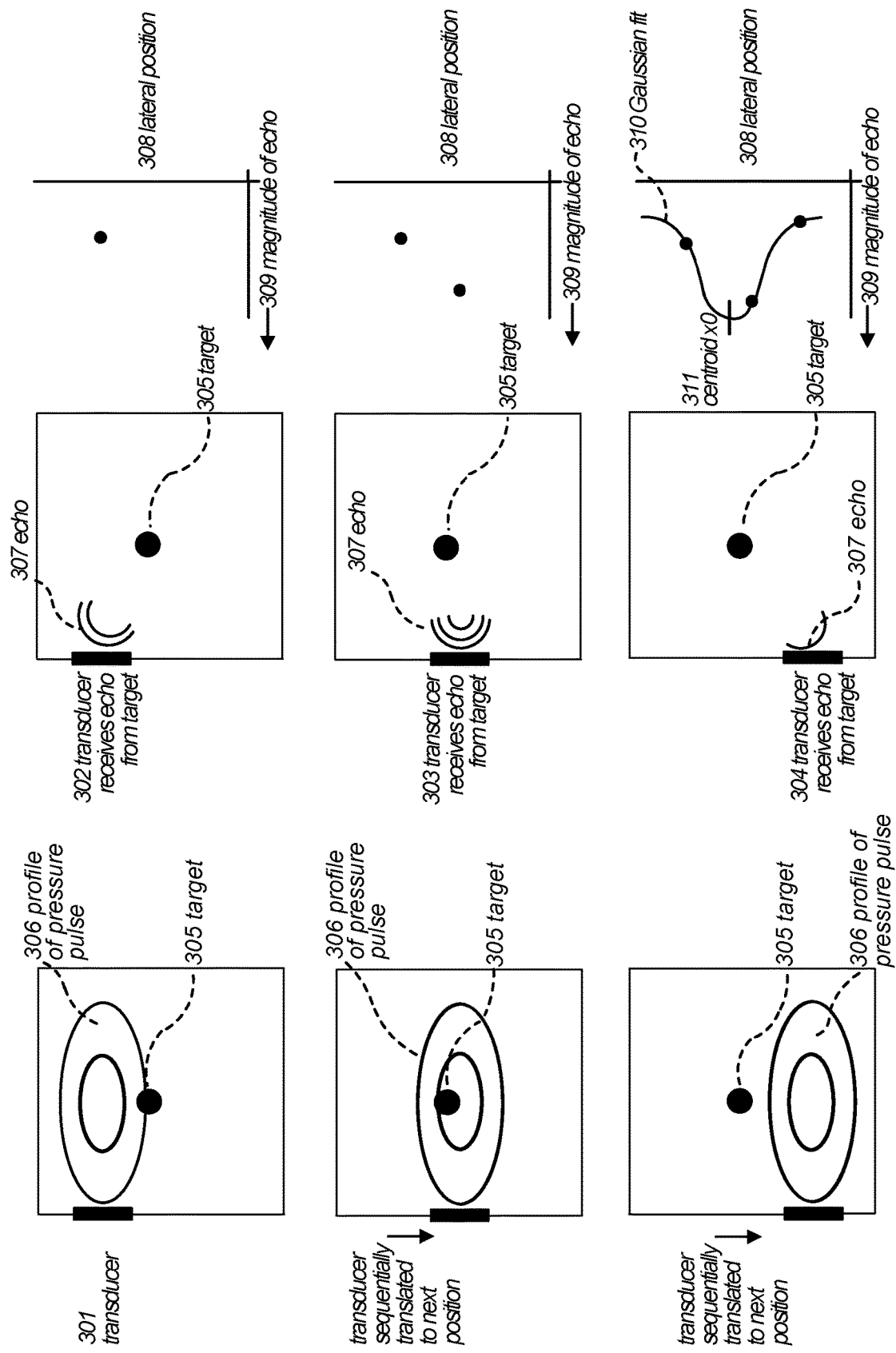
FIG. 3 is a schematic representation of pulse-echo convolution for target location.

An exemplary use of the device for detection of a target in situ is further illustrated in FIG. 3. A transducer 301 transmits pulses of ultrasonic energy 310 having a width (FWHM) and depth across an anatomical region exterior to an interior anatomical region possibly containing an echogenic object of interest 305. In some embodiments, the target is selected from the group consisting of a kidney stone, a gall stone, a region of tissue calcification, a region of calcification or other biomineralization, a foreign object of sufficiently different acoustic impedance than a natural tissue, and an accumulation of contrast agents. In some embodiments, the contrast agents are materials having a specific affinity to a tissue, a cell, an organ, a foreign object, a kidney stone, a gall stone, or an atheromatous plague. In some embodiments, the contrast agents are microbubbles. The microbubbles can be administered to the subject before detection of the target.

For a target with effective diameter phi [T], for FWHM>phi[T], the echo from each sequential reflection is detected by a sensing transducer (e.g., a hydrophone) 302, 303, 304 within the acoustic treatment assembly. In some embodiments, one transducer is used both as the sensing transducer and the excitation transducer. A plurality of ultrasound beams 306 are transmitted from a transducer and plurality of echoes 307 are received as the transducer sequentially moves to the next positions. As a consequence of the longer wavelength and its associated decrease in spatial resolution, the reflected signal (echoes 307) will have a broader distribution (referred to as the point-spread-function, or PSF). However, the PSF is still concentric with the center of the target such that mapping this intensity profile allows a determination of the location of the target with higher precision than is possible with a single measurement. As illustrated in the figure, the ensemble of sequential echo magnitudes 309 within each pulse-echo measurement forms a distribution 310 which is concentric with the location of the target 305 (i.e., target), 311 (i.e., centroid). In some embodiments, the distribution is Gaussian 310 as presented in FIG. 3, or overlapping Gaussian or Airy function distribution.

This ensemble analysis method and algorithm can be more accurate (proportional to the square root of the number of samples in the lateral dimension) at localizing the target than an individual measurement (which is limited by both the broad beam width and the precision in position and alignment of the treatment assembly) and furthermore are amenable to in situ alignment of the treatment assembly and target via feedback.

In some embodiments, the reflected component of the ultrasound beams received by the sensing transducer is analyzed by a processor to calculate a position of the target. In some embodiments, the processor is a part of a detection device comprising the excitation transducer and/or the sensing transducer. In some embodiments, the processor is a part of a separate computing device. In some embodiments, the processor measures a temporal delay between emissions of acoustic pulses by the excitation transducer and receptions of the reflected component of the acoustic pulses by the sensing transducer. The temporal delays can be used to determine the position of the target relative to the excitation transducer or the sensing transducer. Sometimes, the amplitudes of the reflected component of the ultrasound beams are used to determine the position of the target.

In some embodiments, the processor sends the information related to the position of the target to an output device. In some embodiments, the output device is a display device that displays the information related to the position of the target as a text, as a sound or visual signal, or as an image. In some embodiments, the output device generates a report related to the position of the target. In some embodiments, the processor saves the information related to the position of the target in a storage device for later use.

In some embodiments, the processor can analyze variations of amplitudes of the emitted pulses of ultrasonic energy and the received, reflected component of the pulses of ultrasonic energy. Sometimes, the analyzed variations are used to determine the position and presence of the target or the Mie-scatterer.

E. Systems and Methods for Aligning Transducers

In some embodiments, a user can use the information related to the position of the target to rotate or translate the excitation transducer to align it to the target for subsequent detection. In some embodiments, the information related to the position of the target is sent to a device configured to rotate or translate the excitation transducer to be aligned to the target for subsequent detection.

In some embodiments, a user can use the information related to the position of the target to rotate or translate a sensing transducer to align it to the target for subsequent detection. In some embodiments, the information related to the position of the target is sent to a device configured to rotate or translate the sensing transducer to be aligned to the target for subsequent detection. In some embodiments, the excitation transducer can emit pulses of ultrasonic energy only when it is aligned with a target.

In some embodiments, a user can use the information related to the position of the target to rotate or translate a treatment transducer to align it to the target for treatment. In some embodiments, the information related to the position of the target is sent to a device configured to rotate or translate the treatment transducer to be aligned to the target for treatment. In some embodiments, the sensing transducer can receive echo only when it is aligned with a target.

In some embodiments, a treatment transducer emits beams with energy sufficient to break a target such as a kidney stone, a gall stone, a region of tissue calcification, a region of calcification or other biomineralization, a foreign object of sufficiently different acoustic impedance than tissue, an accumulation of contrast agents (targeted or untargeted). In some embodiments, the target is coated with microbubbles. The treatment transducer can emit energy to cause cavitation of the microbubbles that releases sufficient energy to break the target. In some embodiments, a treatment transducer can emit beams with a high energy only when it is aligned with a target.

In some embodiments, one transducer works both as an excitation transducer and a treatment transducer. In some embodiments, one transducer works as an excitation transducer, a sensing transducer and a treatment transducer. In some embodiments, one transducer works as a sensing transducer and a treatment transducer.

Figure 4:
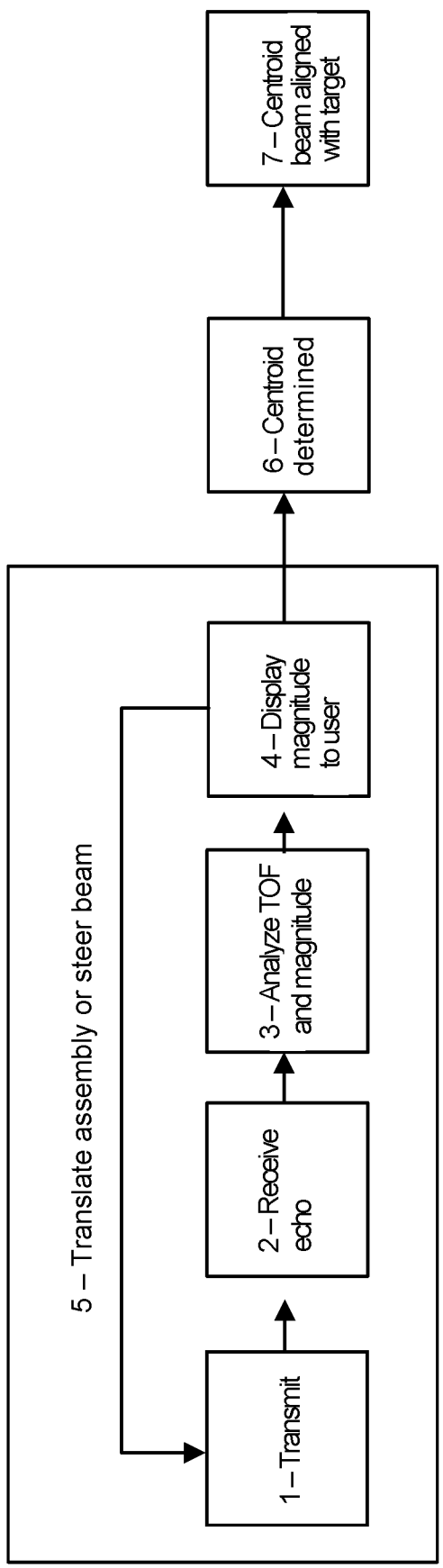
FIG. 4 is a process flow diagram for locating a target by pulse-echo convolution with a translating or steered weakly focused beam.

FIG. 4 summarizes an exemplary method of using low frequency ultrasound for target detection. First, an excitation transducer transmits low frequency ultrasound beams (1). In certain locations, a component of the low frequency ultrasound beam is reflected from a target. A sensing transducer (e.g., a hydrophone) receives echo reflected from the target (2). A processor determines the TOF (time-of-flight) to window the echo and measures the magnitude of the echo using various methods known in the art and/or described herein (3). The magnitude is displayed to a user and/or stored for later use (4). The user or a machine can translate or steer the beam for sequential measurement (5). A processor can analyze and map the magnitude information and determine a centroid of the received signals (6). Information related to the centroid can be used by the user or a device to steer or translate the treatment assembly to be aligned with the target (7).

Figure 5A:
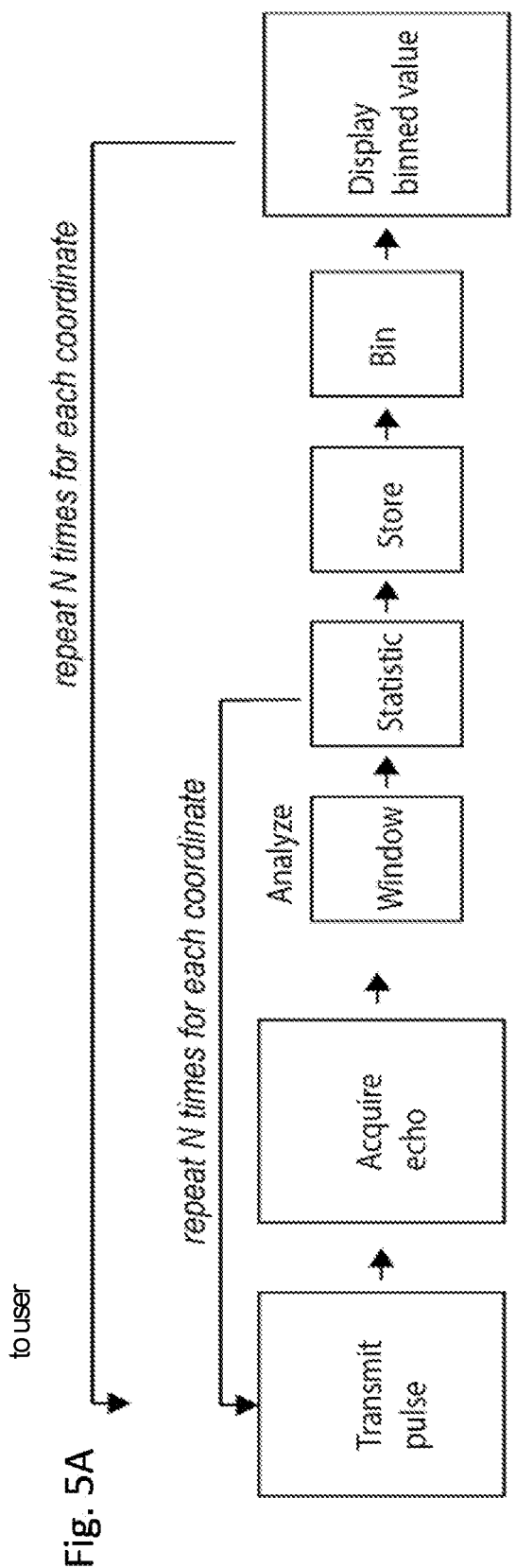
FIG. 5A is a process flow diagram of possible target detection algorithm using low frequency ultrasound.

FIGS. 5A and B further provide flowcharts summarizing two possible target detection algorithms using low frequency ultrasound. The first method summarized in FIG. 5A involves transmission of a short pulse 501, followed by a period of acquisition 502 by the detector. Echoes acquired during the acquisition period are analyzed 503, for example, to determine the time-of-flight of all reflected signals. Next, the acquired data is windowed for the time-of-flight of interest, a statistic 504 of merit of the windowed data is recorded, and the value is stored 505. This loop can repeat certain number of times (N) 508 to account for motions due to respiration. From this ensemble of measurements, a statistical representation can be chosen for the collected data, the result is binned 506 and then displayed 507 to the user in real-time. In this algorithm, it is the user who finds the appropriate alignment by varying the appropriate coordinate, guided by the displayed data output.

Figure 5B:
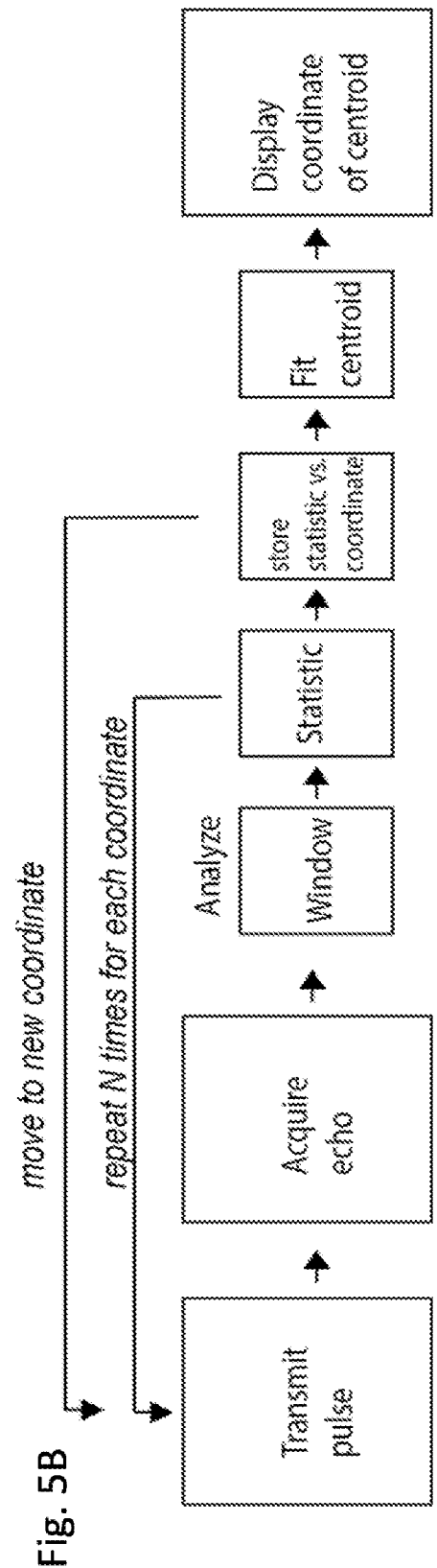
FIG. 5B is a process flow diagram of another possible target detection algorithm involving measurement at multiple coordinates.

The second method summarized in FIG. 5B is similar to the first method with one major difference—after certain number of cycles are processed for a given coordinate and stored, additional cycles are stored for different coordinate values 518. While varying the coordinates, the acquired data for a given coordinate can be stored and compared 514 with stored data for different coordinates. This process allows the distribution of collected data to be processed electronically so that the centroid of the distribution can be determined 515 and displayed 516 to the user.

F. Advantages of the Present Invention

Figure 6:
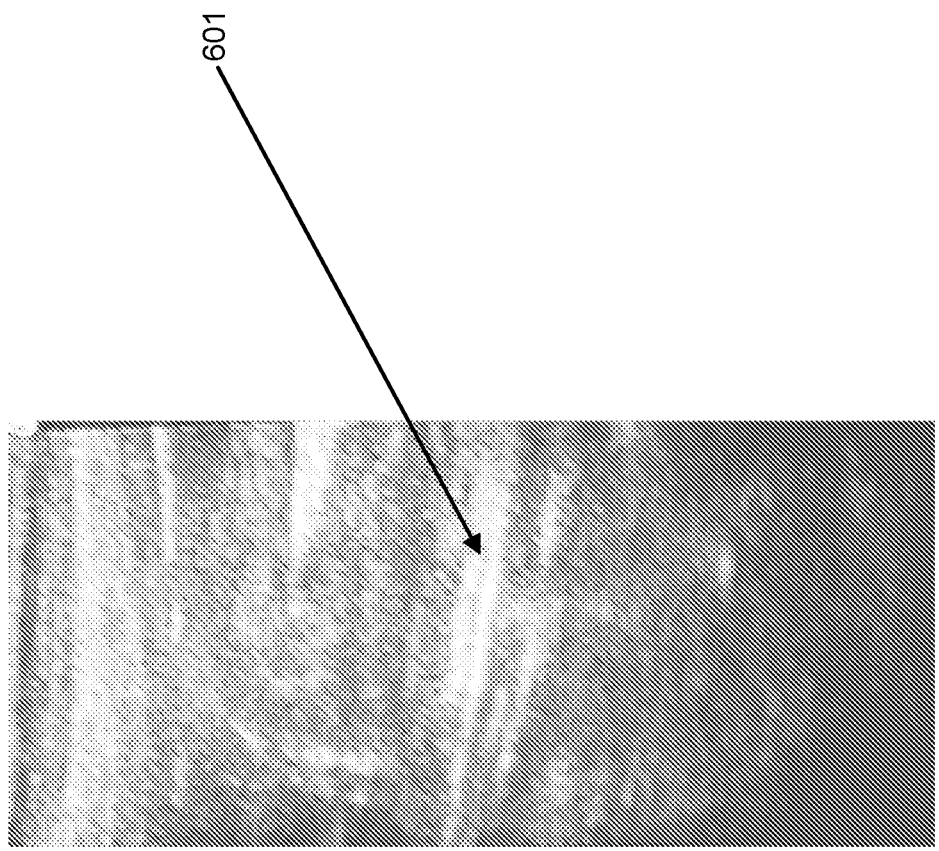
FIG. 6 represents a 2D cross-section of a torso imaged in real-time in situ with high-frequency ultrasound.

FIG. 6 provides a 2D cross-section of a torso imaged in real-time in situ with high-frequency ultrasound representing the current state of the art. The vertical axis represents depth from the skin or the surface, and the horizontal dimension represents a dimension orthogonal to the surface. A poor signal-to-noise ratio, as illustrated in this figure, requires the use of imaging and pattern recognition to distinguish features and interpret the structure. It also requires analysis and interpretation by an experienced sonographer because the cellular structure of the tissue is very reflective to ultrasound as well. In this particular example, the object was identified by the sonographer as a kidney stone 601.

As illustrated herein, the present invention allows alignment of an ultrasound beam for the purpose of treatment and therapy without the use of a separate imaging system or the use of anatomical landmarks for navigation. Imaging techniques can be quite precise (e.g., x-ray CT) but if the generated image is then projected back onto the patient via anatomical landmarks, as is common practice, in order to align an ultrasound treatment transducer with a target, then all that precision goes straight out the window.

Furthermore, the present invention showed that there are competitive advantages in choosing a lower frequency that contributes to reduce background noise—the lower frequency both (1) penetrates soft tissue more easily (less absorption) allowing for deeper detection, and (2) is scattered by the soft tissue back towards a detector to less of a degree.

G. EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed.

I. Example 1: In Vitro Target Detection

Figures 7A, 7B:
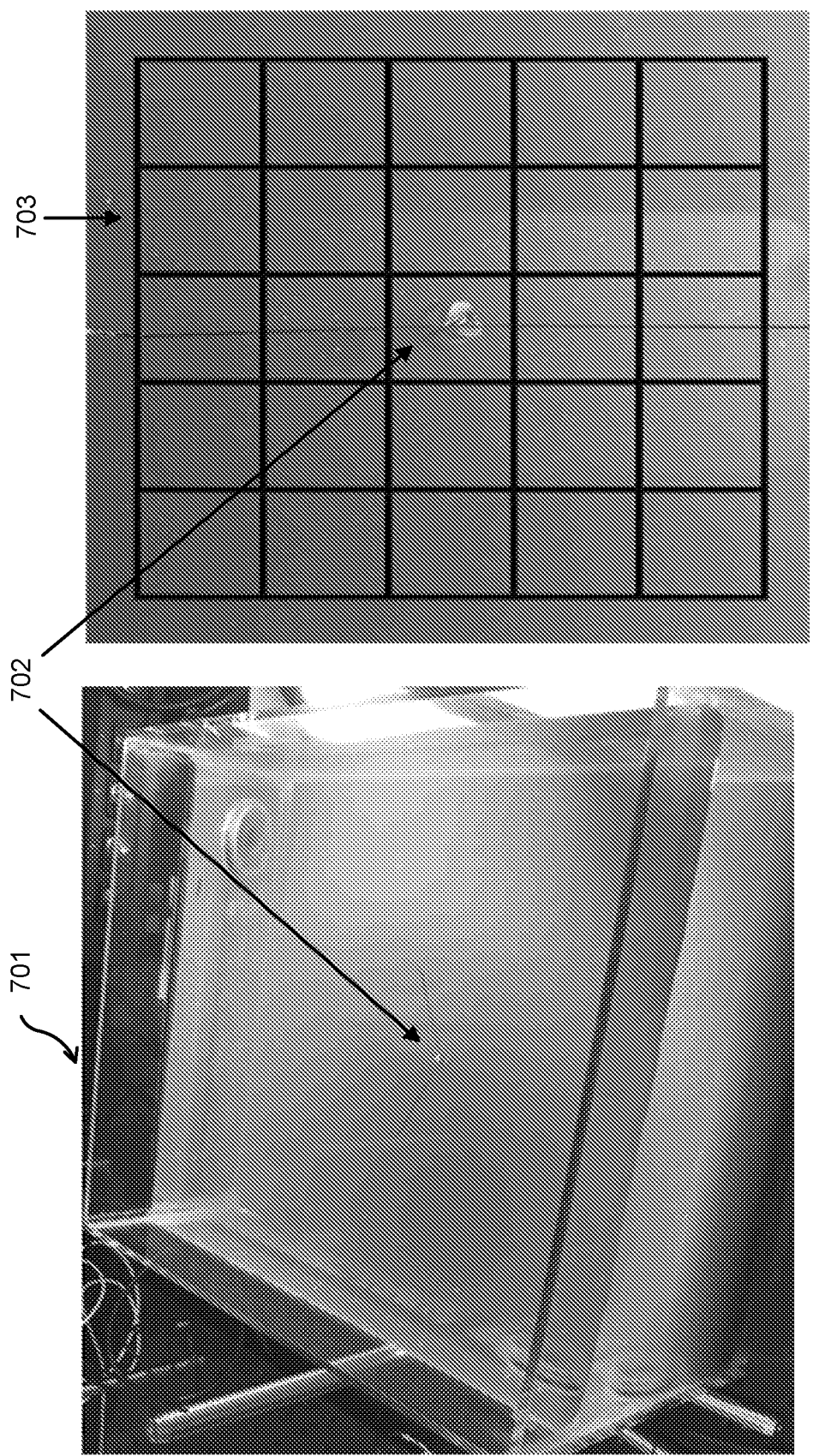
FIG. 7A and FIG. 7B illustrate an example of a target in a tissue phantom for testing the present invention in vitro.

The present invention has been demonstrated using tissue phantoms described in FIGS. 7A and B. FIG. 7A is a photo of a plexiglass chamber 701 filled 8 cm deep with a gelatin matrix. The gelatin matrix functions as a tissue phantom. A target 702 is suspended in the gelatin matrix to represent a target of interest. While a variety of targets could be used for demonstration, lead pellets are a suitable choice given lead's ultrasonic energy reflective properties. A layer of water above the gelatin aids in coupling between the transducer head and the gelatin. FIG. 7B shows a top view of experimental set-up with a size 5 (7.5 mm diameter) lead pellet 702 as the target. A 5×5 cm grid 703 has been superimposed on the photograph.

Figure 8:
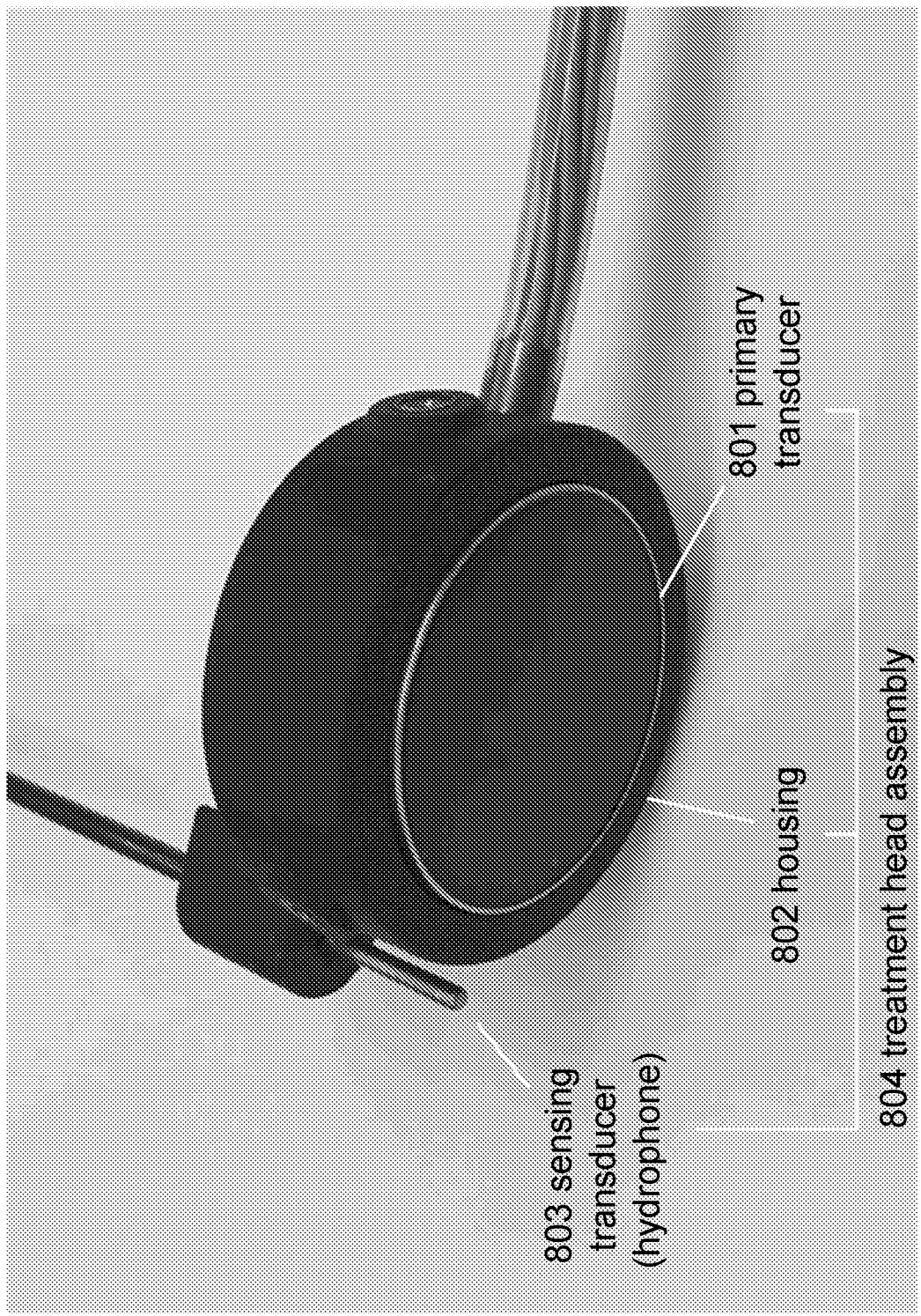
FIG. 8 is a photograph of an exemplary excitation transducer capable of producing weakly focused beams affixed to a sensing transducer (hydrophone).

As shown schematically in FIG. 8, an ultrasonic transducer 801, referred to as a primary transducer, was configured in a housing 802. The primary transducer incorporates multiple elements that are capable of being driven incoherently by independently operational linear amplifiers, so that acoustic energy waves emitted by the active elements by the primary transducer constructively and destructively interfere to produce a weakly focused beam, in this case an approximately cylindrical beam of acoustic energy, sometimes referred to as a collimated beam. The primary transducer can comprise an excitation transducer and a treatment transducer. The primary transducer can also comprise one transducer, that can work both as an excitation transducer and a treatment transducer.

A second transducer, referred to as a sensing transducer 803, is positioned alongside the excitation transducer in the housing 802. With the active regions of the primary transducer 801 and the sensing transducer 803 aligned, the time elapsed between the origination of the pulse at the primary transducer face and the arrival of the echo at the sensing transducer is approximately the time-of-flight of the echo ($\delta t$), and can be related to the total distance ($\delta x$) between the transducer-hydrophone and the object by:

$$\delta x = (c \cdot \delta t)/2 \qquad \text{Equation [2]}$$

where c is the speed of sound in the matrix. The housing 802, primary transducer 801, and sensing transducer 803 collectively constitute a treatment head assembly 804.

The treatment head assembly 804 was positioned above the gelatin matrix and scanned in both x and y at 1 cm increments across the 5×5 cm grid 703. The resulting pulse-echo data was then analyzed for amplitude and plotted.

Emitted signal is a small number of ultrasound pulses (5 cycles, 580 kHz, 1.1 MPa). The target used here is a lead lure, which is slightly asymmetric. Signal reflections from this target are expected to be higher intensity than that of a natural kidney stone (reflection coefficients are compared below) by a factor of 2 to 4, depending on the kidney stone composition. However, this can be compensated for by going to higher transmitted pressures.

The shape of the profile echo distributed across the grid (PSF, shown above) is due to a combination of an interference pattern from the reflection at the target and the detection geometry. Although the distribution above is peaked in the center, the distribution can be more complicated due to the physics of wave interference patterns generated by a target that is a comparable size to the wavelength of the sound wave.

Figure 9A:
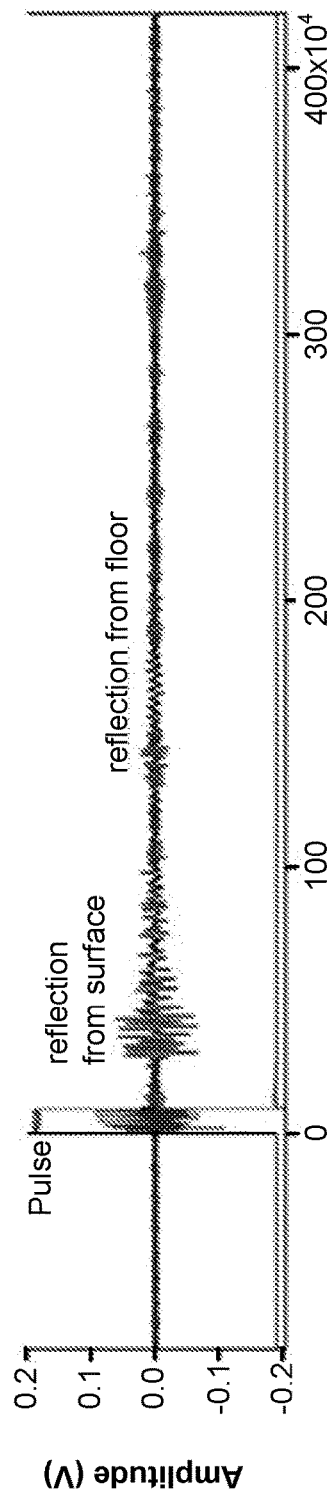
FIGS. 9A, 9B and 9C show representative pulse-echo data from experiments using an exemplary ultrasound device.
Figure 9B:
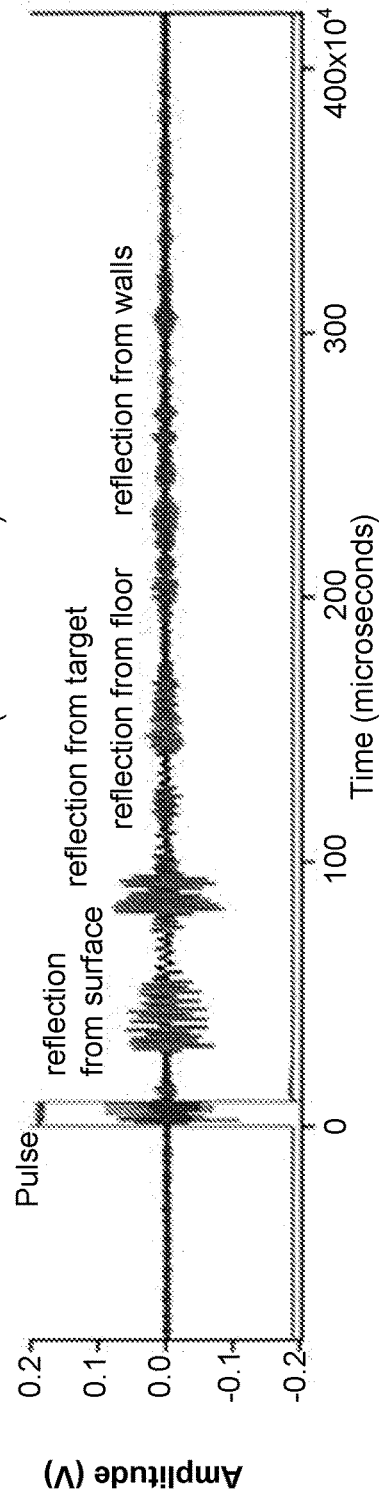
Figure 9C:
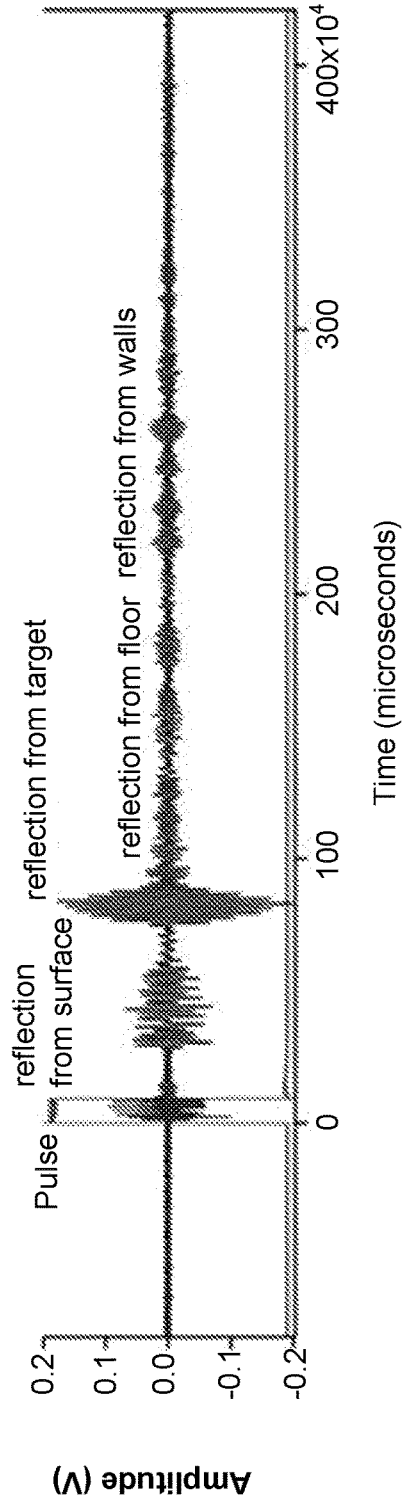

Representative pulse-echo data are reproduced in FIGS. 9A-C. In every case, the pulse on-time is shown at t=20 microseconds. The sensing transducer traces show echoes from reflective surfaces within the path of the beam. At around t=140 microseconds, echoes from the walls and floor of the chamber 701 begin to arrive at the sensing transducer 803. FIG. 9A shows a trace of echoes representing a complete miss of a target. FIG. 9B shows a trace of echoes representing a glancing (partial) reflection from a target. FIG. 9C shows a trace of echoes representing a direct hit to a target.

The maximum amplitude of the acoustic echo inside the window of 1.4 ms to 3.4 ms is plotted as a function of position in FIG. 10A. Although the point-spread-function for the reflection is more complex than presented here, a symmetric function such as Gaussian can be used to estimate the centroid of the distribution (in analogy to optics, where an Airy distribution can be approximated as a Gaussian for the purpose of finding the centroid). In this specific example, the sequential data from the echo was fitted to a 2D Gaussian distribution which included parameters which localize the centroid (x0,y0). This was done with the knowledge that the distribution of the echo sound wave (i(x)) was strongly determined by the Gaussian beam produced by the transmitter. Although the exact functional form of the blurring function was not calculated a priori, the use of a Gaussian was consistent with the major contribution to the blurring function being the Gaussian distribution in the transmit beam width. As shown in FIG. 10B, fitting the array of maximum amplitude values to a 2D Gaussian results in an estimate of the centroid of the distribution and therefore the position of the target with respect to the surface; the fit estimates the centroid to within 0.2 cm of the center of the "0 cm" square, which is within experimental error for this experiment.

II. Example 2: In Vivo Target Detection

The present invention has been further demonstrated in an alive 30 kg swine model (FIG. 14A) implanted with a stone as described in R. F. Paterson et al., Percutaneous stone implantation in the pig kidney: a new animal model for lithotripsy research, J. Endourol., 16:8, 543-547, (2002).

Specifically, a 4 mm cysteine kidney stone was inserted in the proximal ⅓ of the right ureter of a live pig using a catheter to place it. The depth of the ureter was verified to be approximately 3.5±0.5 cm below skin using diagnostic ultrasound to visualize the depth of the catheter sheath inserted into the ureter. The sheath was then retracted before beginning echolocation.

Figure 11B:
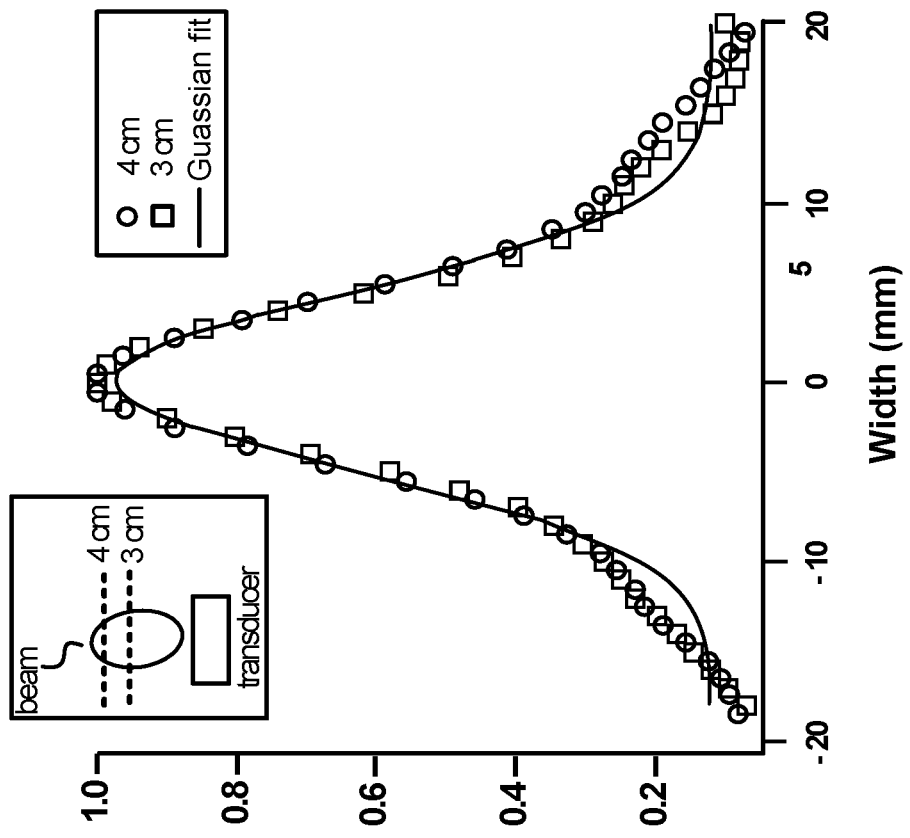
FIG. 11B provides normalized pressure amplitudes measured in the 3 cm and 4 cm depth.
Figure 11A:
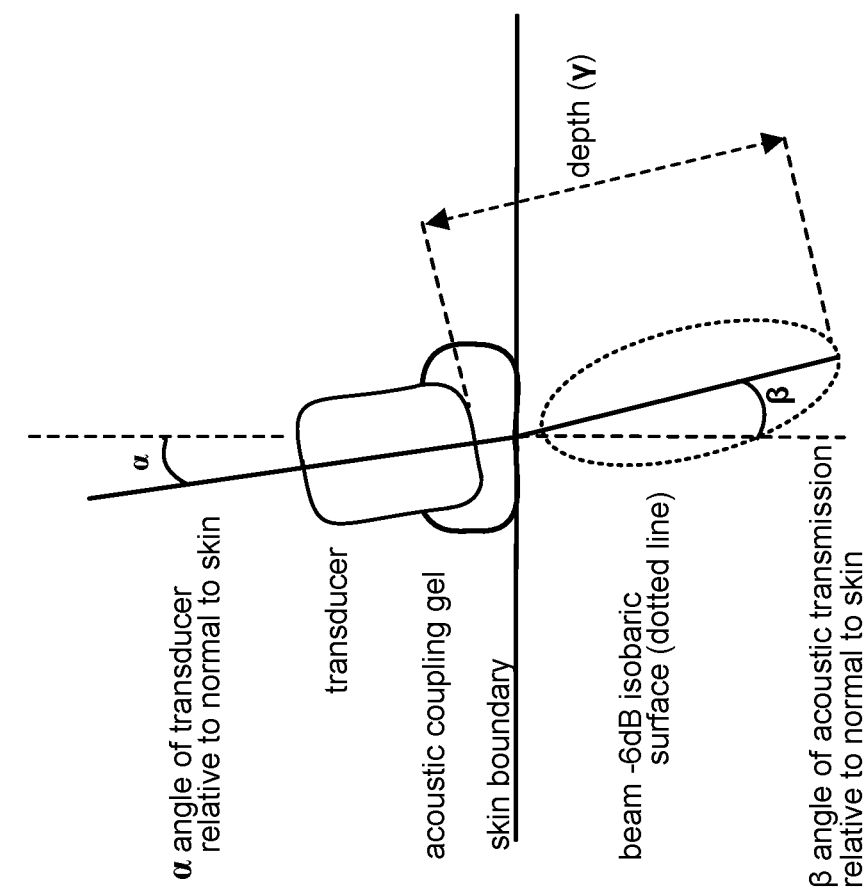
FIG. 11A is a diagram of subcutaneous application of ultrasound in the swine model summarized in Example 2.

As illustrated in FIG. 11A, acoustic coupling gel (Aquasonic) was used in a thick layer to couple both the transducer and the hydrophone of the device while rotating along each axis, which produced an additional stand-off from the surface of between 1 and 5 mm. A 10 microsecond duration pulse was transmitted using a planar 25 mm square transducer driven at 75 W electrical power at a frequency of 580 kHz. A model for subcutaneous ultrasound transmission where the transducer is held an angle α is provided in FIG. 11A, where 6 dB isobaric surface of the ultrasound pressure (volume) is presented as a dotted ellipsoid. The resulting in vivo acoustic axis ((β) may differ from α.

The subcutaneous pressure delivered in the 3 to 4 cm depth from the skin was between 1 and 1.1 MPa, as verified by a hydrophone in a degassed water tank. The beam width from the 13 mm wide square transducer drive at 580 kHz was measured at 3 cm and 4 cm in profile using a hydrophone in a degassed water tank. Pressure amplitudes measured in the 3 (open circles) or in the 4 cm depth (open rectangles) are provided in FIG. 11B.

The electrical trigger was recorded to calculate the time-of-flight of the reflected echoes. The echoes were recorded using a mounted needle hydrophone (Y104, from Sonic Concepts, approximately 6V/MPa transfer function at 580 kHz), with a 10× gain pre-amplifier (SRS 983). A clinometer with 0.1 degree accuracy (Johnson Level) was used to measure the angle with respect to the skin surface.

FIGS. 12A and B provide representative pressure echoes (kPa) versus depth from the skin (y) measured for α=−4 degrees (FIG. 12A) and α=−15 degrees (FIG. 12B) along the cranial-caudal axis. The time of flight from the recorded pressure wave was converted to depth using an approximate coverage speed of sound (1500 m/s), and therefore represents an approximate depth. The recorded pressure echoes are also presented as a function of angle (α, degrees) with respect to the surface along two axes—the cranial-caudal (FIG. 13A) and the dorsal-ventral (FIG. 13B).

Pressure echoes (e.g., FIGS. 12A/B and 13A/B) were recorded in triplicate for each angle relative to normal to the skin, to improve sampling during breathing. The received data were windowed to round-trip time-of-flights between 26 μs to 66 μs, corresponding to a range in depth of 2 cm to 5 cm. The maximum value of the windowed data was recorded with its accompanying angle of measurement. The maximum values were then binned into three bins: 0 to 90 kPa, 90 to 120 kPa, and 120 kPa to 150 kPa and assigned a color: white, gray, and black, respectively and presented on the cranial-caudal, and the dorsal-ventral axes in FIG. 14B. The axes investigated are overlaid on a pig in FIG. 14A.

The dorsal-ventral scan revealed only background reflections without highly reflective peaks, as illustrated in FIGS. 13B and 14B. In contrast, the cranial-caudal scan shows a region of high reflectivity, as provided in FIGS. 13A and 14B (the black box). Fitting the reflected echoes to a Gaussian produced a fit with a centroid of $x_0$=−3.4657 degrees±0.38 degrees, a half-width=2.5202±0.574 mm and a constant background of $y_0$=52.61±2.31 kPa. The total transverse sub-cutaneous distance examined via angular displacements for the object 4 cm below the skin was 3 cm along the dorsal-ventral axis, and 2 cm along the cranial-caudal axis.

The region of highly reflective peaks, from 0 degrees to −5 degrees in the cranial-caudal scan, shows higher variation in the data, with a standard deviation of 22.5 kPa, corresponding to 23% variation in the average value. In contrast, the region of low reflectivity, e.g. from 1 degree to 15 degrees in the cranial-caudal scan, is of lower variation in reflectivity and also displays a tighter standard deviation of 7.85 kPa, corresponding to 13% of the average. This increased variability, as measured by the standard deviation, is interpreted as the signature of increased angular sensitivity, as expected from scattering from an object in the Mie regime. Although exact angular dependences of Mie-scattering cross-sections changes with size and reflection coefficient, it is in all cases sharper than the cosine dependence of a planar geometrical interface. Chapter 7, More and Ingard (1968) *Theoretical Acoustics*.

Thus, this analysis could verify the location of the kidney stone, consistent with it's a priori placement.

In some cases, this algorithm may be automated to give real-time feedback, with the color bins corresponding to indicator lights. Furthermore, the device can be translated as well as tilted to aid in location while scanning the entire ureter.

III. Example 3: Verification of In Vivo Target Detection

Analysis of the Reflected Pressure Distribution:

Given the small size of the kidney stone relative to the transmitted beam-width, the blurring function or point-spread-function (PSF) distribution of the reflected sound wave should be dominated by the beam-width of the transmitted beam. The transmitted beam-width can best be described by a solution to the diffraction equation, e.g. Somerfield-Rayleigh equation or Fresnel-Kirchhoff equation, but is typically fitted by a Gaussian to good approximation, as is widespread practice in optical applications. At a depth of 4 cm, the transmitted beam width fits a Gaussian with beam half-width of approximately 12 mm (FIG. 11B).

At a depth of 4 cm, the 12 mm transmit beam-width corresponds to approximately 16 degrees of angle α. An additional consideration is the transmission angle from the coupling gel to the skin. Acoustic coupling gels are made of proprietary mixtures, intended for matching the acoustic impedance to skin in the diagnostic regime, where acoustic impedance is a function of the product of the speed of sound to the density. Acoustic gel has been observed to vary by several percent in transmission rate for different. Furthermore, since the product of density and speed of sound are matched, the speed of sound is not independently matched.

The consequence of variation in the speed of sound at the acoustic gel/skin interface is that the angle of transmission will also be affected. For example, a 30% difference in the speed of sound will result in an approximately 30% change in angle, and 6 degree incident angle (α) to normal may result in a 8 degree transmission angle (β).

While the echogenic data as a function of angle does not span 16 degrees in width, but rather 6 to 8 degrees of width, the difficulty in achieving exact numerical agreement, especially in precise aiming, in the presence of respiratory movements is widely understood, and typically handled through removal of data affected by respiratory movements. Although an exact model for the effect of respiratory motion is not available, the increased variation in peak pressure observed in the window α=−5 to 1 degrees (30% variation, versus 20% variation outside this window) is consistent with the challenges of achieving exact numerical agreement, and supports the approach of taking multiple measurements to reduce the error in the measurement.

Verification of the Reflected Pressure Amplitude:

Assuming perfect pointing alignment, the expected amplitude of an echo can be estimated from considerations of each source of attenuation:

$$P_{echo} = (P_{in})(L)(A)(R)(D) \quad \text{Equation [3]}$$

Where, $P_{echo}$=pressure received from echo
$P_{in}$=initial pressure pulse from the transducer
L=spherical spreading loss from reflection on spherical surface
A=attenuation from media (tissue) for a given path length
R=reflection coefficient at kidney stone interface, or scattered from microbubbles
D=directivity of the receiver Equation [3] is based on the foundational Sonar Equation governing echolocation, with Pout corresponding to echo strength, $P_{in}$ to transmitted signal level, L and A to transmission losses from spreading and attenuation, and R to target strength. The receiver focus or Directivity (D) is approximated as unity, due to the needle hydrophone used in the current embodiment having negligible angular dependence in the range considered in this study. The noise level, or background, is considered separately.

The coefficient of transmission T for the gel-tissue interface is approximated as unity, and therefore omitted from equation [3], however, angular dependences on the transmission angle will be considered separately. Furthermore, alternative paths involving reflections and reverberations are not considered. Implicit in the calculation of L and R is that the kidney stone is spherical, which is not an unreasonable approximation given that, at this frequency, the wavelength and kidney stone diameter are comparable in size. Implications of this approximation are remarked upon below.

Geometrical Dissipation Due to Spherical Spreading Loss

The echogenic pressure decreases with distance as it propagates back:

$$\frac{I}{I_a} = \frac{r^2}{R^2} \cos^2\theta \quad \text{Equation [4]}$$

where $I_a$ is the reflected acoustic intensity, r is the radius of the target (ureteral kidney stone) and R is the distance from the kidney stone to the receiver, θ is the angle of the transducer with respect to the line-of-slight to the kidney stone. For the angles presented herein the cosine dependence is negligible, and the pressure should go as the square root of the intensity, which simplifies to:

$$\frac{P}{P_a} = \frac{r}{R} \quad \text{Equation [5]}$$

Where Pa is the reflected pressure amplitude, and $P_0$ is the incident pressure amplitude. For R=4 cm to 15 cm, the resulting attenuation would be a factor of L=0.125 to 0.03, respectively, representing the largest contribution to attenuation of the echo intensity in equation [3].

Attenuation/Dissipation $$D(d) = \frac{P}{P_0} = e^{-\alpha f d} \quad \text{Equation [6]}$$

where a is the attenuation coefficient, f is the frequency, d is the distance traveled, and $P_0$ is the pressure at d=0. The attenuation coefficient for tissue is 0.5 dB MHz$^{-1}$ cm$^{-1}$. For a round-trip path length of 2×4 cm to 2×15 cm (twice the minimum and maximum depth of a kidney stone), this would produce an attenuation factor in tissue of D=0.8 for 4 cm to 0.4 for 15 cm, respectively.

Reflection from Kidney Stones

The fraction of reflected pressure for a wave normal to an interface can be calculated from the reflection coefficient:

$$R = \frac{P_r}{P_i} = \frac{z_1 - z_2}{z_2 + z_1} \quad \text{Equation [7]}$$

The reflection from a cysteine kidney stone is approximately R~0.8 for an acoustic impedance of Z=8. Combining the above numbers for a kidney stone of 4 cm into equation [3] produces an estimated echo:

$$P_{echo} = (1.1 \text{ MPa})(0.125)(0.8)(0.8)(1) = 8 \text{ kPa}.$$

Note that the observed peak amplitude (140 kPa, FIG. 13A) is comparable to this value when the background is considered (30 to 50 kPa). This rough agreement is all the more impressive considering the implicit assumption in the calculation of L and R that the scattering cross-section of the target can be described by the geometrical cross-section. It is noted that the true scattering cross-section in the Mie-regime ($1<2\pi a/\lambda<10$) can result in a scattering cross-section that is either higher or lower than the geometrical cross-section of the target.

Resolution and SNR of the Measurement

The measured centroid of the target, found by fitting to a Gaussian in FIG. 13A, is $x_0=-3.4657$ degrees±0.38 degrees. This is a more precise localization than the diffraction limit for a 580 kHz acoustic beam ($\lambda/2=1.29$ mm), which is $\tan^{-1}(2.58 \text{ mm}/4 \text{ cm})=1.85$ degrees. In addition, this is more precise localization than the limit imposed by the transmitted beam width or insonation volume, as described by the F number times the wavelength (Fk=6.5 mm, or 9.2 degrees).

In contrast to conventional diagnostic ultrasound imaging, which is limited in special resolution by the wavelength of the transmitted ultrasound beam, this technique is limited by the number of measurements taken. Adapting an analogous optical limit on localization to acoustics gives:

$$\langle(\Delta x)^2\rangle = \frac{s^2}{N} + \frac{8\pi s^4 b^2}{N^2}$$

where Δx is the error in localization along one dimension, s is the standard deviation of the distribution, N is the number of measurements recorded, and b is the standard error in the background noise normalized by the dimension of the receiver. Note that the uncertainty due to the number of measurements falls as $1/\sqrt{N}$ for the signal and $1/N$ for the background.

We are justified in setting this sensitivity due to the resolution in the hydrophone sensitivity, which is 6V/MPa. Assuming a 1 mV resolution with 20-fold gain, the amplitude resolution can be as low as 10 Pa. However, the SNR (signal-to-noise-ratio) will be determined by the background from reflections of other subcutaneous features, such as tissue interfaces. This highlights an advantage to operating in the sub-MHz regime. By lengthening the wavelength of the transmitted acoustic wave, the wavenumber ($2\pi/\lambda$) is reduced and the 'speckle' background due to diffuse scattering off of concentrated living cells in tissue is reduced.

As an example of the expected reflectivity of a tissue interface, consider the lining of the ureter, which is composed of smooth muscle immediately adjacent to an aqueous lumen giving rise to a reflection coefficient ($Z_1$=1.69 MRayl for muscle, $Z_2$=1.48 MRayl for water) of R=0.066, nearly 10% of the value of the reflection coefficient for the ureteral kidney stone. The cylindrical shape of the ureter in humans is approximately 5 mm in diameter, and considering the background from the two interfaces on each side of the lumen, this would set a SNR of 5. Other surfaces may also contribute, including interfaces between skin and fat, muscle and fat, etc.

IV. Example 4: Target Detection Using Contrast Agents

The present invention allows in situ location of a material with sufficient echogenicity over surrounding tissue, which includes contrast agents such as microbubbles disclosed in U.S. Pat. No. 9,329,260 B2 or Errico et al, Ultrafast ultrasound localization microscopy for super-resolution vascular imaging, NATURE, 527, 499-502 (2015). (doi:10.1038/nature16066). The contrast agents can be injected into a region of interest.

The targeted microbubbles can contain a tag which binds preferentially to a target. The contrast agent is injected into a region of interest. After sufficient incubation period, the unbound contrast agent is removed via washes or natural circulation processes. Such a technique is applied intravenously to detect calcium deposits in the circulatory system. The present method can be applied to locate the target of interest, which may include calcified tissue, without the use of anatomical landmarks or imaging techniques.

Once located, the presence of the targeted contrast agent is quantified to ascertain the abundance of the target. The present invention can be also used to detect leakage of a tissue or organ, such as the detection of pericardial effusion in the abdomen, by detecting an increase in width of the distribution relative to an expected width.

Additionally, once located the present method can be applied to align an ultrasound beam for the purpose of treatment and therapy without the use of a separate imaging system or the use of anatomical landmarks for navigation.

For example, contrast agents can be injected into a ureter. Pulse-echo data can be taken for a tiled array of values. The distribution of values can form a 1D Gaussian transverse to the ureter, but produce an approximately constant value in the direction axial to the ureter. The data can be used to align a treatment ultrasound transducer to the ureter for treatment by aligning the transducer to the center of the Gaussian distribution in the transverse direction.

V. Example 5: Treatment Using Targeted Microbubbles

Microbubbles disclosed in U.S. Pub. No. 20130123781 are also used as contrast agents. The microbubbles selectively adhere to positively charged calcium-containing materials, such as kidney stones. The microbubbles are injected into a region of interest. After sufficient incubation period, the unbound microbubbles are removed via washes or natural circulation processes. Once the location of the microbubbles is determined as described herein, a treatment transducer is aligned to the microbubbles attached to the target. The therapeutic ultrasound transducer transmits sufficient energy targeted to the microbubbles to break apart the target, e.g., kidney stones, into smaller particles.

The same transducer can emit both low frequency ultrasound for detection and ultrasound for therapeutic applications. This integration further simplifies the process of alignment for targeted application of high frequency beams.

VI. Example 6: Treatment of Cardiovascular Disease

The invention can be used as part of a program of treatment of cardiovascular disease associated with biomineralization. For example, aortic valve stenosis is a condition often requiring surgery. For a patient with a degree of stenosis of significant clinical concern but with factors disfavoring surgery, a weakly focused ultrasound beam can be used to treat stenosis. Such treatment of stenosis can be carried out either with or without the use of microbubbles introduced into the vicinity of the aortic valve.

Microbubbles introduced into the vicinity of the aortic valve can incorporate targeting moieties specific for calcium associated with the stenosis.

5. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

6. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A system for locating a target in situ cornprising:
an excitation transducer emitting pulses of ultrasonic energy waves having one or more frequencies ranging from 100 kHz to 1 MHz, wherein an average wavelength of said ultrasonic energy waves is greater than a size of the target,
wherein said ultrasonic energy waves are approximately collimated in a volume beginning at least 3 cm away from an aperture and extending at least 4 cm away from the aperture; and
a sensing transducer receiving a component of the pulses of said ultrasonic energy waves emitted by said excitation transducer after reflection from the target,
wherein said component of the pulses of said ultrasonic energy waves has an average wavelength greater than the size of the target and is related to a position of the target.

2. The system of claim 1, wherein the emitted pulses of the ultrasonic energy waves provide a non-derated instantaneous pressure at a point with an (x, y, z) coordinate, wherein the non-derated instantaneous pressure deviates less than 6 dB from a non-derated instantaneous pressure at a different point with an (x, y, z') coordinate,
wherein each of the (x, y, z) and (x, y, z') is a coordinate of a point within the volume,
z' is a value between 3 cm and 10 cm, and
z and z' are a value for a coordinate axis normal to the aperture face.

3. The system of claim 1, further comprising a moving part configured to rotate or translate the excitation transducer.

4. The system of claim 1, further comprising a processor that operates on the received, reflected component of the pulses of the ultrasonic energy waves and outputs a signal related to the position of the target.

5. The system of claim 4, further comprising a treatment aligner that aligns a treatment transducer based on the signal related to the position of the target.

6. The system of claim 5, wherein the treatment transducer emits energy to the target.

7. The system of claim 6, wherein the energy emitted from the treatment transducer has a magnitude sufficient to cause breakage of the target.

8. The system of claim 5, wherein the excitation transducer and the treatment transducer are same.

9. The system of claim 4, wherein the processor further measures a temporal delay between emission of pulses of the ultrasonic energy waves by the excitation transducer and reception of the reflected component of the pulses of the ultrasonic energy waves by the sensing transducer.

10. The system of claim 9, wherein the temporal delay is used to determine the position of the target relative to the excitation transducer.

11. The system of claim 9, wherein the temporal delay is used to determine the position of the target relative to the sensing transducer.

12. The system of claim 4, wherein the processor decides the position of the target based on amplitudes of the received, reflected component of the pulses of the ultrasonic energy waves.

13. The system of claim 1, wherein the excitation transducer and the sensing transducer are same.

14. The system of claim 1, wherein the received, reflected component of the pulses of the ultrasonic energy waves is not used to generate an image of the target.

15. The system of claim 1, wherein the pulses of the ultrasonic energy waves emitted from the excitation transducer have different amplitudes.

16. The system of claim 1, wherein the pulses of the ultrasonic energy waves emitted from the excitation transducer have different frequencies.

17. The system of claim 1, wherein maximum amplitude values of the received, reflected component of the pulses of the ultrasonic energy waves form a distribution, wherein a centroid of the distribution correlates with a center of the target.

18. The system of claim 17, wherein the distribution of maximum amplitude values is Gaussian, overlapping Gaussian or Airy function distribution.

19. The system of claim 1, wherein an average frequency of the pulses of the ultrasonic energy waves emitted from the excitation transducer ranges from 500 kHz to 600 kHz.

20. The system of claim 19, wherein an average frequency of the pulses of the ultrasonic energy waves emitted from the excitation transducer ranges from 550 kHz to 600 kHz.

21. The system of claim 1, wherein a resolution of the system $\Delta R$ is larger than 0.5 mm,
wherein the $\Delta R$ is calculated as:

$$\Delta R = \lambda F,$$

wherein $\lambda$ is an average wavelength of the pulses of the ultrasonic energy waves emitted from the excitation transducer, and
F is a ratio of the aperture's focal length to the aperture's diameter or the excitation transducer's F-number.

22. The system of claim 21, wherein the $\Delta R$ is larger than 1 mm.

23. The system of claim 22, wherein the $\Delta R$ is larger than 2.5 mm.

24. The system of claim 23, wherein the $\Delta R$ is larger than 5 mm.

25. The system of claim 1, wherein at least 80% of the ultrasonic energy waves emitted from the excitation transducer are confined to the volume with a lateral width ranging from 1 cm to 4 cm.

26. The system of claim 25, wherein at least 90% of the ultrasonic energy waves emitted from the excitation transducer are confined to the volume with a lateral width ranging from 1 cm to 4 cm.

27. The system of claim 26, wherein at least 95% of the ultrasonic energy waves emitted from the excitation transducer are confined to the volume with a lateral width ranging from 1 cm to 4 cm.

28. The system of claim 1, wherein the target is selected from the group consisting of a kidney stone, a gall stone, a foreign object of sufficiently different acoustic impedance than a natural tissue, and an accumulation of contrast agents.

29. The system of claim 28, wherein the target is an accumulation of contrast agents, wherein the contrast agents have a specific affinity to a tissue, a cell, an organ, a foreign object, a kidney stone, a gall stone, or an atheromatous plague.

30. The system of claim 28, wherein the contrast agents are microbubbles.

31. The system of claim 28, wherein the target is a kidney stone.

32. The system of claim 28, wherein the target is a gall stone.

33. A method for locating a target smaller in situ, comprising the steps of:
emitting pulses of ultrasonic energy waves having one or more frequencies ranging from 100 kHz to 1 MHz by an excitation transducer, wherein an average wavelength of said ultrasonic energy waves is greater than a size of the target,
wherein said ultrasonic energy waves are approximately collimated in a volume beginning at least 3 cm away from an aperture and extending at least 4 cm away from the aperture; and
receiving, by a sensing transducer, a component of the pulses of the ultrasonic energy waves emitted by said excitation transducer after reflection from the target, wherein said component of the pulses of the ultrasonic energy waves has an average wavelength greater than the size of the target and is related to a position of the target.

34. The method of claim 33, wherein the emitted pulses of the ultrasonic energy waves provide a non-derated instantaneous pressure at a point with an (x, y, z) coordinate,
wherein the non-derated instantaneous pressure deviates less than 6 dB from a non-derated instantaneous pressure at a different point with an (x, y, z') coordinate,
wherein each of the (x, y, z) and (x, y, z') is a coordinate of a point within the volume,
z' is a value between 3 cm and 10 cm, and
z and z' are a value for a coordinate axis normal to the aperture face.

35. The method of claim 33, wherein the step of emitting pulses of the ultrasonic energy waves is done while moving the excitation transducer along the surface of a torso of a mammalian subject.

36. The method of claim 33, further comprising the steps of operating on the received, reflected component of the pulses of the ultrasonic energy waves and outputting a signal related to the position of the target.

37. The method of claim 36, further comprising a step of aligning a treatment transducer based on the signal related to the position of the target.

38. The method of claim 37, further comprising a step of emitting energy from the treatment transducer to the target.

39. The method of claim 38, wherein the energy emitted from the treatment transducer has a magnitude sufficient to cause breakage of the target.

40. The method of claim 37, wherein the excitation transducer and the treatment transducer are same.

41. The method of claim 33, wherein the excitation transducer and the sensing transducer are same.

42. The method of claim 33, wherein the received, reflected component of the pulses of the ultrasonic energy waves is not used to generate an image of the target.

43. The method of claim 33, further comprising the step of measuring a temporal delay between emission of the pulses of the ultrasonic energy waves by the excitation transducer and reception of the reflected component of the pulses of the ultrasonic energy waves by the sensing transducer.

44. The method of claim 43, wherein the temporal delay is used to determine the position of the target relative to the excitation transducer.

45. The method of claim 43, wherein the temporal delay is used to determine the position of the target relative to the sensing transducer.

46. The method of claim 33, further comprising the step of determining the position of the target based on amplitudes of the received, reflected component of the pulses of the ultrasonic energy waves.

47. The method of claim 33, wherein the pulses of the ultrasonic energy waves emitted from the excitation transducer have different amplitudes.

48. The method of claim 33, wherein the pulses of the ultrasonic energy waves emitted from the excitation transducer have different frequencies.

49. The method of claim 33, wherein maximum amplitude values of the reflected component of the pulses of the ultrasonic energy waves form a distribution, wherein a centroid of the distribution correlates with a center of the target.

50. The method of claim 49, wherein the distribution of maximum amplitude values is Gaussian distribution, overlapping Gaussian or Airy function distribution.

51. The method of claim 33, wherein an average frequency of the pulses of the ultrasonic energy waves emitted from the excitation transducer ranges from 500 kHz to 600 kHz.

52. The method of claim 51, wherein the average frequency of the pulses of the ultrasonic energy waves emitted from the excitation transducer ranges from 550 kHz to 600 kHz.

53. The method of claim 33, wherein at least 80% of the ultrasonic energy waves emitted from the excitation transducer are confined to the volume with a lateral width ranging from 1 cm to 4 cm.

54. The method of claim 52, wherein at least 90% of the ultrasonic energy waves emitted from the excitation transducer are confined to the volume with a lateral width ranging from 1 cm to 4 cm.

55. The method of claim 33, wherein a resolution of the system $\Delta R$ is larger than 0.5 mm,
wherein the $\Delta R$ is calculated as:

$$\Delta R = \lambda F,$$

wherein $\lambda$ is an average wavelength of the pulses of the ultrasonic energy waves emitted from the excitation transducer, and
F is a ratio of the aperture's focal length to the aperture's diameter or the excitation transducer's F-number.

56. The method of claim 55, wherein the $\Delta R$ is larger than 1 mm.

57. The method of claim 56, wherein the $\Delta R$ is larger than 2.5 mm.

58. The method of claim 57, wherein the $\Delta R$ is larger than 5 mm.

59. The method of claim 54, wherein at least 95% of the ultrasonic energy waves emitted from the excitation transducer are confined to the volume with a lateral width ranging from 1 cm to 4 cm.

60. The method of claim 33, wherein the target is selected from the group consisting of a kidney stone, a gall stone, a foreign object of sufficiently different acoustic impedance than a natural tissue, and an accumulation of contrast agents.

61. The method of the claim 60, wherein the target is a kidney stone.

62. The method of claim 60, wherein the target is an accumulation of contrast agents, wherein the contrast agents are designed to specifically adhere to a tissue, a cell, an organ, a foreign object, a kidney stone, a gall stone, or an atheromatous plague.

63. The method of claim 62, wherein the contrast agents are microbubbles.

64. The method of claim 63, further comprising the step of administering the microbubbles to a mammalian subject.

65. The method of claim 33, further comprising the steps of analyzing variations of amplitudes of the emitted pulses of the ultrasonic energy waves and the received, reflected component of the pulses the ultrasonic energy waves, and identifying a Mie-scatterer based on the variations.

\* \* \* \* \*